United States Patent
Davis et al.

(10) Patent No.: US 11,045,278 B2
(45) Date of Patent: *Jun. 29, 2021

(54) CLEANING DEVICE AND METHOD FOR USING THE SAME

(71) Applicant: NEOMED, INC., Woodstock, GA (US)

(72) Inventors: Benjamin M. Davis, Woodstock, GA (US); Aaron N. Ingram, Canton, GA (US); David A. Doornbos, Woodstock, GA (US)

(73) Assignee: NeoMed, Inc., Woodstock, GA (US)

( * ) Notice: Subject to any disclaimer, the term of this patent is extended or adjusted under 35 U.S.C. 154(b) by 135 days.

This patent is subject to a terminal disclaimer.

(21) Appl. No.: 16/223,917

(22) Filed: Dec. 18, 2018

(65) Prior Publication Data
US 2019/0117332 A1    Apr. 25, 2019

Related U.S. Application Data

(63) Continuation-in-part of application No. 15/938,607, filed on Mar. 28, 2018, now Pat. No. 10,888,393,
(Continued)

(51) Int. Cl.
*A61B 90/70* (2016.01)
*B08B 1/00* (2006.01)
(Continued)

(52) U.S. Cl.
CPC ............. *A61B 90/70* (2016.02); *A46B 9/02* (2013.01); *A61J 15/0026* (2013.01);
(Continued)

(58) Field of Classification Search
CPC ............. A61J 15/0026; A61B 90/70; A61B 2090/701; A61M 2209/10; A61M 39/16;
(Continued)

(56) References Cited

U.S. PATENT DOCUMENTS

| | | |
|---|---|---|
| 1,523,754 A | 1/1925 | Chippeaux |
| 1,710,127 A | 4/1929 | Vaughn |
| (Continued) | | |

FOREIGN PATENT DOCUMENTS

| | | |
|---|---|---|
| DE | 2020090090081 U1 | 9/2009 |
| JP | 2001309973 A | 4/2003 |

OTHER PUBLICATIONS

Capture of Youtube video of use of EnClean brush (previously cited by applicant) having a date of Sep. 11, 2015 (Year: 2015).*
(Continued)

*Primary Examiner* — Mark Spisich
(74) *Attorney, Agent, or Firm* — Dority & Manning, P.A.

(57) ABSTRACT

A cleaning device for cleaning a connector comprising a lumen and an inner threaded surface. The cleaning device includes a cleaning body and a plunger body operably coupled to each other. The cleaning body includes a plurality of elongated cleaning swabs positioned separately apart from and in parallel to each other. The plurality of elongated cleaning swabs are operably rotatable about a connector lumen and in removable engagement with a connector inner threaded surface. The plunger body includes an elongated plug to removably engage the connector lumen. The cleaning body and the plunger body are translatably coupled along a common operational axis. The cleaning body and the plunger body are rotatably coupled with respect to each other about the common operational axis. The cleaning body is an integral structure.

19 Claims, 25 Drawing Sheets

Related U.S. Application Data which is a continuation of application No. 15/009,073, filed on Jan. 28, 2016, now Pat. No. 9,931,176.

(60) Provisional application No. 62/599,912, filed on Dec. 18, 2017, provisional application No. 62/108,824, filed on Jan. 28, 2015.

(51) Int. Cl.
| | |
|---|---|
| *A46B 9/02* | (2006.01) |
| *B08B 9/027* | (2006.01) |
| *A61J 15/00* | (2006.01) |
| *A61M 5/00* | (2006.01) |
| *A61M 39/16* | (2006.01) |
| *A61M 39/20* | (2006.01) |

(52) U.S. Cl.
CPC ............ *A61M 5/001* (2013.01); *A61M 39/16* (2013.01); *B08B 1/002* (2013.01); *B08B 1/003* (2013.01); *B08B 1/006* (2013.01); *B08B 9/027* (2013.01); *A46B 2200/3006* (2013.01); *A46B 2200/3013* (2013.01); *A46B 2200/3073* (2013.01); *A61L 2202/17* (2013.01); *A61L 2202/24* (2013.01); *A61M 39/20* (2013.01); *A61M 2209/10* (2013.01)

(58) Field of Classification Search
CPC ............... A61M 39/20; A61L 2202/10; A61L 2202/17; A61L 2202/20; A61L 2202/24; A61L 2/00; A61L 2/02; A61L 2/16; A61L 2/18; A61L 2/26; A46B 9/00; A46B 9/02; A46B 9/005; A46B 15/00; A46B 2200/30; A46B 2200/3073; A46B 2200/3006; A46B 2200/3013; B08B 1/00; B08B 1/001; B08B 1/002; B08B 1/003; B08B 1/006; B08B 2240/00; B08B 9/00; B08B 9/02; B08B 9/021; B08B 9/023; B08B 9/027

See application file for complete search history.

(56) References Cited

U.S. PATENT DOCUMENTS

| | | | |
|---|---|---|---|
| 1,759,739 A | 5/1930 | Ferris | |
| 2,190,216 A | 2/1940 | Nunziato | |
| 2,629,888 A | 3/1953 | Sauer | |
| 2,893,029 A | 7/1959 | Vosbikian et al. | |
| 3,231,921 A | 2/1966 | Cuervo | |
| 3,317,944 A | 5/1967 | Napier, Sr. et al. | |
| 4,575,892 A | 3/1986 | Ross | |
| 5,123,763 A | 6/1992 | Simmons | |
| 5,214,820 A | 6/1993 | Shumway et al. | |
| 5,222,271 A | 6/1993 | Eganhouse | |
| 5,564,149 A | 10/1996 | Matesic et al. | |
| 6,202,247 B1 | 3/2001 | Lorenz, Jr. | |
| 6,250,315 B1 | 6/2001 | Ernster | |
| 6,349,443 B1 | 2/2002 | Randoph et al. | |
| 6,363,948 B2 | 4/2002 | Choi | |
| 6,754,932 B2 | 6/2004 | Buzard | |
| 6,935,802 B1 | 8/2005 | Byun | |
| 7,198,611 B2 | 4/2007 | Connell et al. | |
| 7,234,474 B2 | 6/2007 | Byun | |
| 7,526,830 B2 | 5/2009 | Forrest et al. | |
| 7,543,348 B2 | 6/2009 | Le | |
| 7,763,013 B2 | 7/2010 | Baldwin et al. | |
| 8,061,518 B2 | 11/2011 | Shaughness | |
| 8,065,773 B2 | 11/2011 | Vaillancourt et al. | |
| 8,079,106 B2 | 12/2011 | Yang | |
| 8,172,825 B2 | 5/2012 | Solomon et al. | |
| 8,197,749 B2 | 6/2012 | Howlett et al. | |
| 8,214,961 B2 | 7/2012 | Vinci et al. | |
| 8,252,247 B2 | 8/2012 | Ferlic | |
| 8,336,151 B2 | 12/2012 | Kerr et al. | |
| 8,336,152 B2 | 12/2012 | Vaillancourt et al. | |
| 8,388,894 B2 | 3/2013 | Colantonio et al. | |
| 8,407,846 B2 | 4/2013 | Chen et al. | |
| 8,443,480 B2 | 5/2013 | Zaytoun, Jr. | |
| 8,528,147 B2 | 9/2013 | Larsson et al. | |
| 8,740,864 B2 | 6/2014 | Hoang et al. | |
| 8,777,504 B2 | 7/2014 | Shaw et al. | |
| 8,808,637 B2 | 8/2014 | Ferlic | |
| 8,832,894 B2 | 9/2014 | Rogers et al. | |
| 9,167,891 B2 | 10/2015 | Shaughness | |
| 9,931,176 B2 | 4/2018 | Davis et al. | |
| 2008/0052845 A1 | 3/2008 | Djang | |
| 2008/0295281 A1 | 12/2008 | Kumaran | |
| 2010/0050358 A1 | 3/2010 | Kim | |
| 2010/0200017 A1 | 8/2010 | Kerr et al. | |
| 2011/0314619 A1 | 12/2011 | Schweikert | |
| 2012/0024734 A1 | 2/2012 | Shaughness | |
| 2012/0124758 A1 | 5/2012 | Sabisch et al. | |
| 2012/0186032 A1 | 7/2012 | Donohue et al. | |
| 2013/0197485 A1 | 8/2013 | Gardner et al. | |
| 2014/0261558 A1 | 9/2014 | Rogers et al. | |
| 2015/0217106 A1 | 8/2015 | Banik et al. | |
| 2016/0007729 A1 | 1/2016 | Kirkconnell-Shaughness | |
| 2016/0214142 A1 | 7/2016 | Davis et al. | |
| 2017/0042637 A1 | 2/2017 | Reinard et al. | |

OTHER PUBLICATIONS

Bard Site-Scrub; 1 pg; date unknown.
EnClean Brush; 1 pg; date unknown.
New ISO Tubing Connector Standards: A Follow-Up to the Sentinel Event Alert Webinar PowerPoint Presentation; www.jointcommission.org; 50 pgs; Dec. 3, 2014.
New Tube Feeding Connectors Webinar PowerPoint Presentation; www.oley.org; 24 pgs; Jun. 24, 2014.
International Search Report and Written Opinion for PCT/US2019/067063, dated Apr. 29, 2020, 13 pages.

* cited by examiner

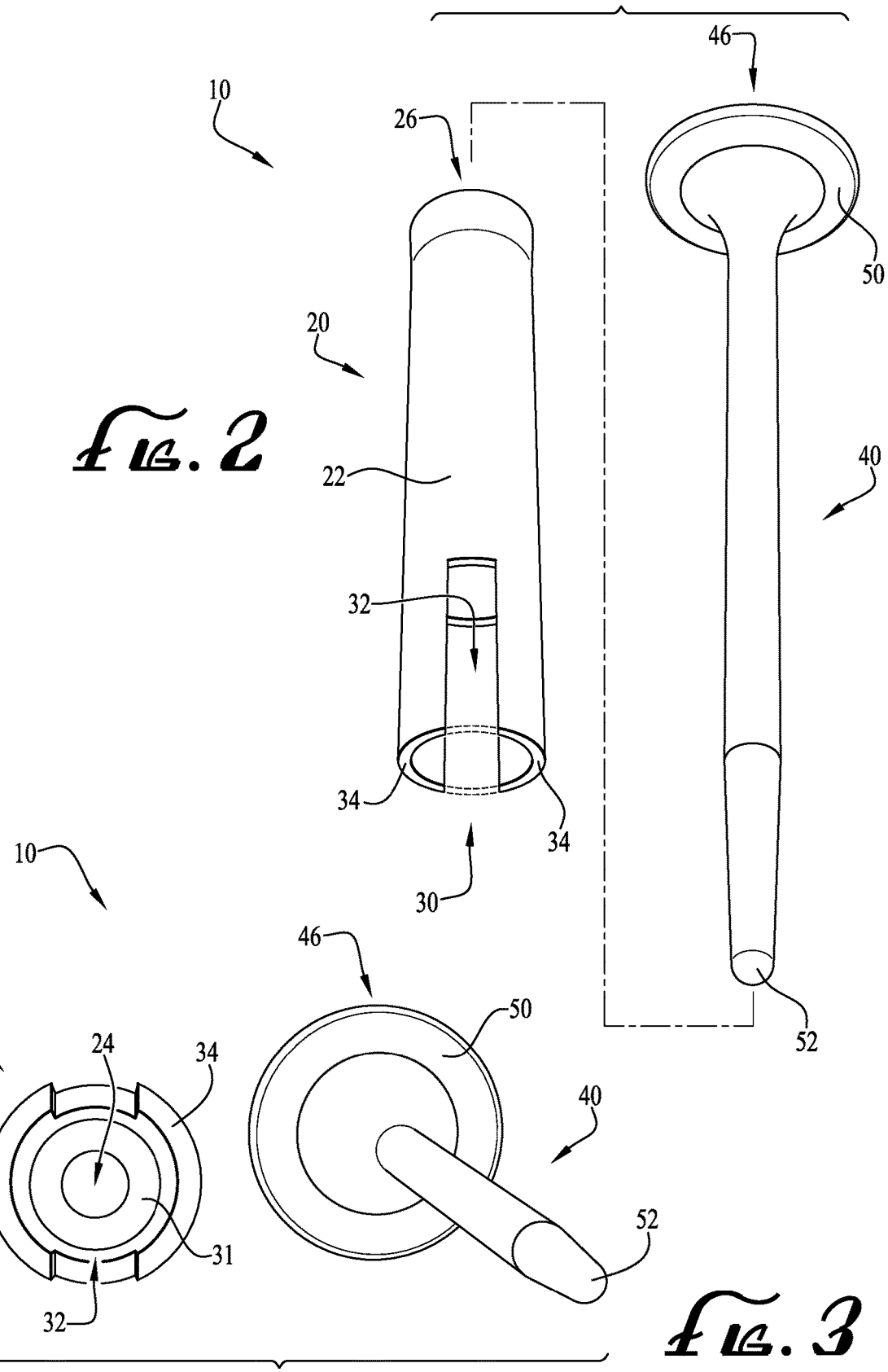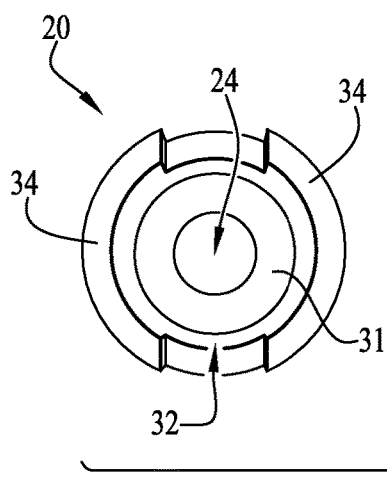

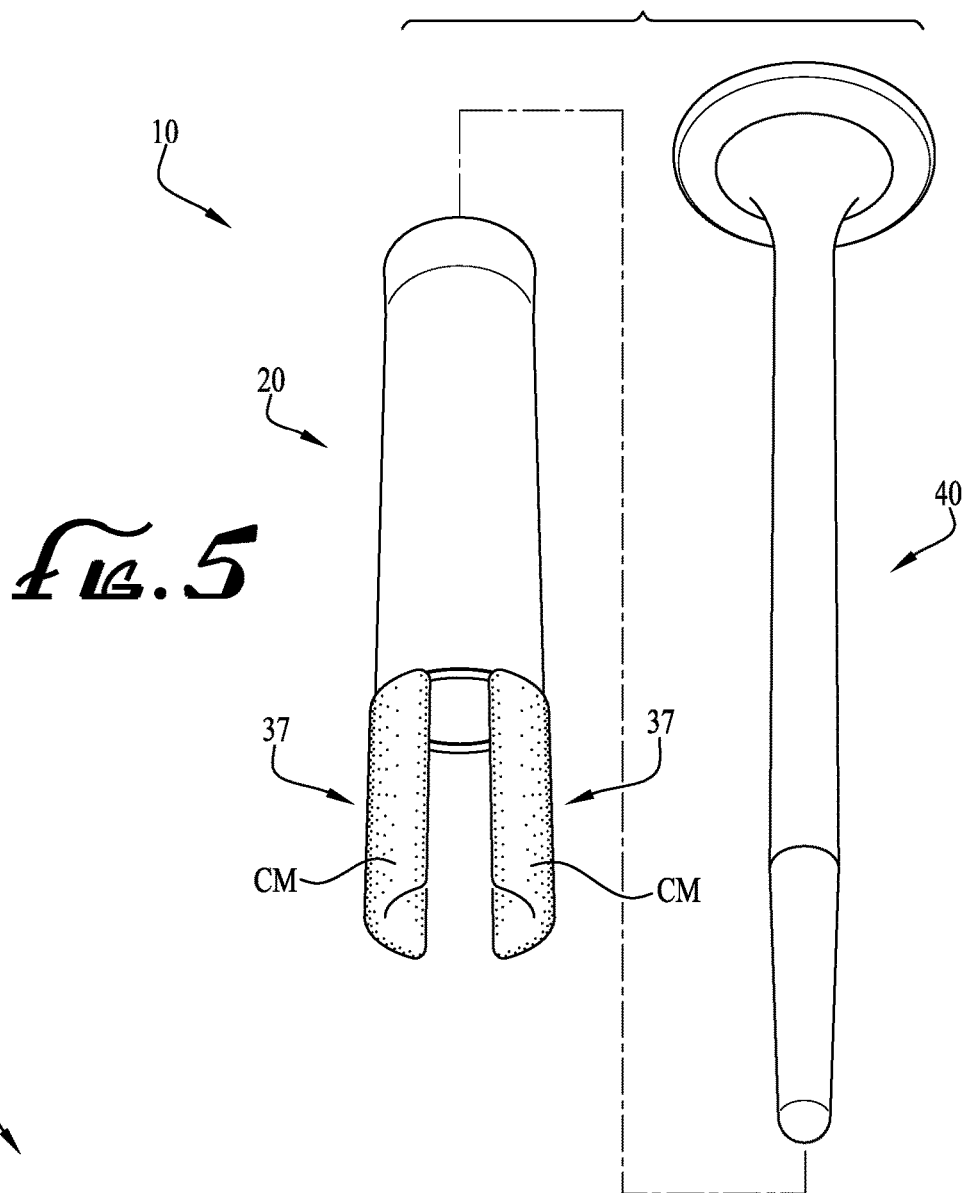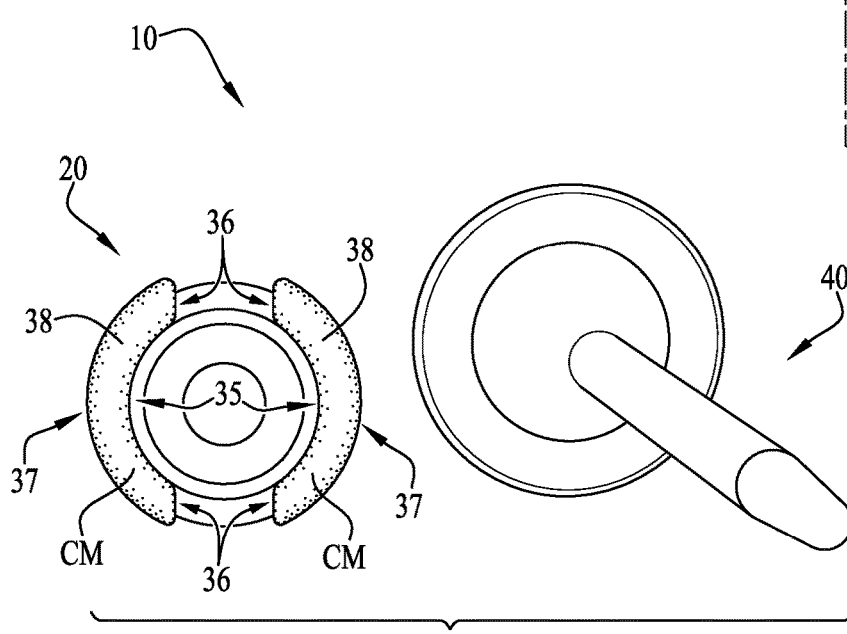

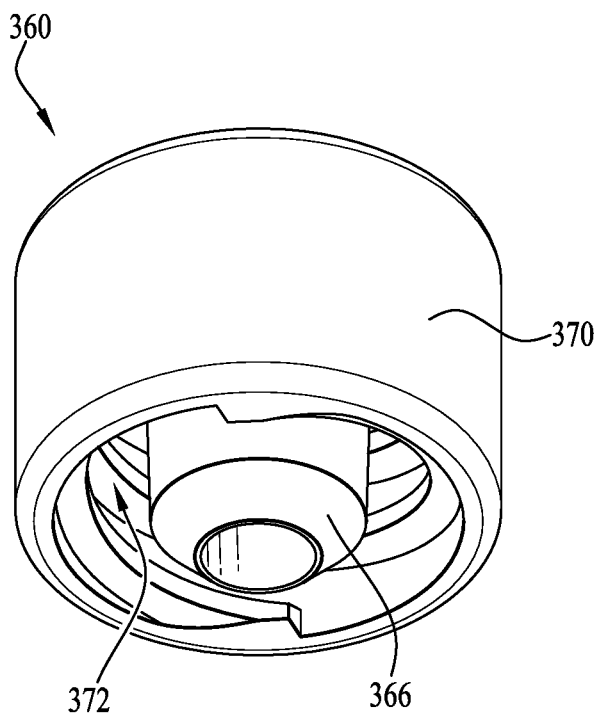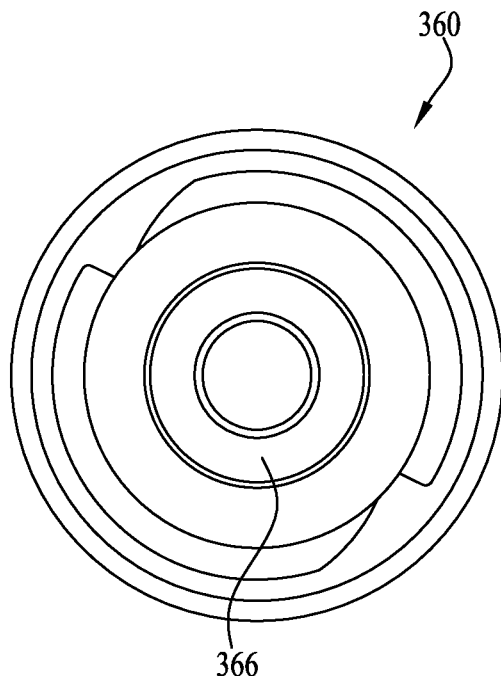
fig. 25A  fig. 25B
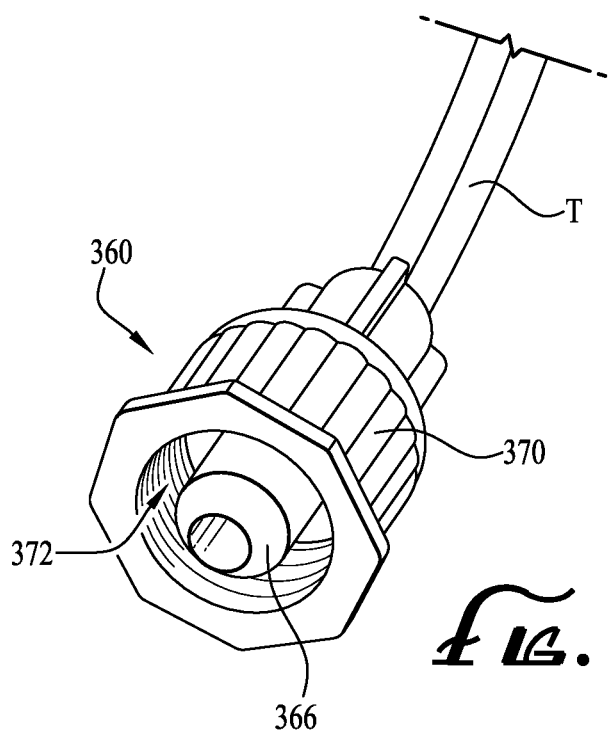
fig. 26

CLEANING DEVICE AND METHOD FOR USING THE SAME

CROSS-REFERENCE TO RELATED APPLICATION

This application is a Continuation-in-Part patent application of U.S. Non-Provisional patent application Ser. No. 15/938,607 filed Mar. 28, 2018, now U.S. Pat. No. 10,888,393, which claims priority to U.S. Non-Provisional patent application Ser. No. 15/009,073 filed Jan. 28, 2016 (now Issued U.S. Pat. No. 9,931,176), which claims priority to U.S. Provisional Patent Application Ser. No. 62/108,824 filed Jan. 28, 2015; and this application also claims the priority benefit of U.S. Provisional Patent Application Ser. No. 62/599,912 filed Dec. 18, 2017; the entirety of each of which is hereby incorporated by reference for all intended purposes.

TECHNICAL FIELD

The present invention relates generally to the field of medical devices, and more particularly to cleaning devices and methods for use with fluid transfer connectors such as coupling connectors for enteral fluid containers.

BACKGROUND

Neonates and other healthcare patients are often administered fluids such as medications, nutritional fluids and supplements via enteral fluid delivery, commonly utilizing delivery systems including fluid containers, syringes, feeding tubes and other components. These components are often interconnected by connectors or couplings such as Luer connectors, or the more recently developed ENFit connector (ISO Standard 80369).

In some embodiments, these enteral connectors or couplings may include outer housing geometries with recesses or areas that could retain small quantities of unused feeding fluids that might allow for bacteria colonization or contain other potential contaminants. U.S. patent application Ser. No. 14/844,956, which is incorporated herein by reference, discloses a vented male ENFit enteral coupling or connector having a housing structure with drainage passages or vents to eliminate or reduce the likelihood of retaining feeding liquids or other contaminants in the outer housing. Further improvements in the field are desirable, and it is to the provision of cleaning swab devices and methods for enteral couplings or connectors that the present invention is primarily directed.

SUMMARY

In example embodiments, the present invention provides cleaning swab devices and methods for cleaning and/or disinfecting fluid transfer connectors or couplings, such as for example enteral feeding couplings. In example forms, the cleaning devices and methods are adapted for application with ENFit fluid transfer connectors in the form of male ENFit connectors, but the devices and methods of the present invention may likewise be adapted to use with other connectors or coupling formats.

In one aspect, the present invention relates to a cleaning device for cleaning a connector, the cleaning device including a generally elongate cylindrical swab member having a first end and a second end, the first end generally opposite the second end, an opening defined within the cylindrical member and extending from the first end to the second end, and a channel formed within a portion of the cylindrical swab member to define at least one finger, the at least one finger preferably comprising a cleaning material to provide for cleaning and/or disinfecting at least a portion of the connector.

In example forms, the at least one finger includes an interior surface, an exterior surface, an intermediate surface, and an end surface. In one example form, at least a portion of one or more of the surfaces are at least partially covered with a cleaning material to provide for cleaning and disinfecting at least portions of the connector. According to example forms, the cleaning material is coated with a cleaning agent in the form of isopropyl alcohol, sterile water, saline, soapy water, or other agent.

In another aspect, the invention relates to a cleaning device for cleaning near and within at least one vent of a vented connector including a generally elongate cylindrical swab member having a first end and a second end, the first end generally opposite the second end, an opening defined within the cylindrical swab member and extending from the first end to the second end, and a channel formed within a portion of the cylindrical swab member to define at least two fingers, the at least two fingers at least partially comprising a material to provide for cleaning and disinfecting at least a portion of the vented connector; and a plunger extending from a first end to a second end, the plunger extending through the opening and comprising an actuating end at the first end and a plug end at the second end.

In example forms, the at least two fingers comprise interior surfaces, exterior surfaces, intermediate surfaces, and end surfaces. In one example form, at least a portion of one or more of the surfaces are at least partially covered with a cleaning material to provide for cleaning and disinfecting at least portions of the vented connector. In another example form, the cleaning material is coated with a cleaning agent in the form of isopropyl alcohol, sterile water, saline, soapy water, or other agent.

In still another aspect, the invention relates to a cleaning device for cleaning and/or disinfecting a connector, the connector including a stem having a lumen extending therethrough, an outer housing, and threads positioned on an internal portion of the outer housing, the cleaning device including a generally elongate tube extending from a first end to a second end and including an opening axially extending therethrough, wherein at least one end of the cleaning device can be inserted between the stem and the threads of the outer housing to clean and disinfect the connector.

In example forms, at least one end of the generally elongate tube includes a channel formed with a portion thereof to define at least one cleaning finger. The at least one cleaning finger includes an interior surface, an exterior surface, an intermediate surface and an end surface. In one example form, one or more of the surfaces are at least partially covered with a cleaning material to provide for cleaning and disinfecting at least portions of the connector.

In yet another aspect, the invention relates to a cleaning device for cleaning and/or disinfecting a connector, the connector including a stem having a lumen extending therethrough, an outer housing, threads positioned on an internal portion of the outer housing, the connector further including a cap having a generally rib-like body, a seal plug extending from the rib-like body, and a tether connecting the cap to the connector, the seal plug generally provided for sealingly engaging the lumen of the stem. The cleaning device includes a generally elongate tube extending from a first end to a second end and having an opening axially extending therethrough, the cleaning device further including a channel formed with a portion of the cylindrical member to define at least one finger, wherein the at least one finger of the cleaning device can be inserted between the stem and the threads of the outer housing to clean and disinfect the connector with or without the seal plug sealingly engaging the lumen of the stem.

In still another aspect, the invention relates to a method of cleaning and/or disinfecting a connector. The connector generally includes a stem having a lumen extending therethrough, an outer housing, and threads positioned on an internal portion of the outer housing. The method includes providing a cleaning device having a generally elongate cylindrical member including a first end and a second end, the first end generally opposite the second end, and an opening defined within the cylindrical member and extending from the first end to the second end; engaging an end of the cleaning device with the connector, the end of the cleaning device generally being positioned between the stem and the threads of the connector; translating and/or rotating the cleaning device relative to the connector while the end of the cleaning device is engaged with the connector; and disengaging the cleaning device from the connector.

In yet another aspect, the invention relates to a cleaning device for cleaning a connector. The cleaning device includes a generally elongate housing, at least one brush member, and a plunger movably mounted to the housing. The housing includes a central opening extending therethrough. The at least one brush member is generally mounted to the housing and is generally laterally offset from the central opening. In example forms, the housing is generally cylindrical in shape and comprises a pair of flanges formed at an end thereof. In example forms, a pair of diametrically opposed channels are defined between the flanges. According to one example form, the at least one brush is mounted to the housing and is recessed within an orifice defined by the flanges, and wherein the channels defined between the flanges allow for the application of a cleaning agent to the at least one brush when a portion of the plunger is engaged with a portion of the connector.

In still another aspect, the present disclosure relates generally to a cleaning device for cleaning a connector comprising a lumen and an inner threaded surface, the cleaning device comprising: a cleaning body and a plunger body operably coupled to each other, the cleaning body comprising a plurality of elongated cleaning swabs positioned separately apart from and in parallel to each other, the plurality of elongated cleaning swabs being operably rotatable about a connector lumen and in removable engagement with a connector inner threaded surface, the plunger body comprising an elongated plug to removably engage the connector lumen; wherein, the cleaning body and the plunger body are translatably coupled along a common operational axis, the cleaning body and the plunger body being rotatably coupled with respect to each other about the common operational axis, and wherein the cleaning body is an integral structure.

In still a further aspect, the present disclosure relates generally to a cleaning device for cleaning a connector comprising a lumen and a threaded inner surface, the cleaning device comprising: an elongated plunger comprising a retained end and a free end, the free end being configured to engage a connector lumen; and a brush body forming a single integral structure, the brush body comprising a gripping portion, a plunger receiver, and a plurality of brushes comprising an elongated post and a plurality of bristles extending therefrom, the plurality of bristles and the elongated plunger being oriented with respect to each other along a common planar axis; wherein the brush body and the elongate plunger are translatably coupled along a common operational axis, the brush body and the elongated plunger being rotatably coupled with respect to each other about the common operational axis.

In still another aspect, the present disclosure relates generally to a method of cleaning a connector comprising a lumen and a threaded inner surface, the method comprising: engaging a plunger body with the connector lumen; engaging a plurality of bristles with the connector threaded inner surface, the plurality of bristles being oriented along a common planar axis; rotating the plurality of bristles with respect to the connector threaded inner surface, and simultaneously rotating the plurality of bristles with respect to the plunger body; and engaging the plurality of bristles with the connector threaded inner surface.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of example embodiments of the invention, and are not restrictive of the invention, as claimed.

BRIEF DESCRIPTION OF THE DRAWINGS

FIG. 2 shows a disassembled perspective view of the cleaning device of FIG. 1.

FIG. 3 shows a front perspective view of the cleaning device of FIG. 1.

FIG. 4 shows the cleaning device of FIG. 1, showing a portion thereof defining an area wherein foam or other cleaning material is applied.

FIG. 5 shows the cleaning device of FIG. 1, indicating a tip portion thereof wherein foam or other cleaning material is applied.

FIGS. 25A-26 show further examples of connectors or couplings to which the cleaning swab assemblies and methods of the present invention may be applied.

DETAILED DESCRIPTION OF EXAMPLE EMBODIMENTS

Figure 1:
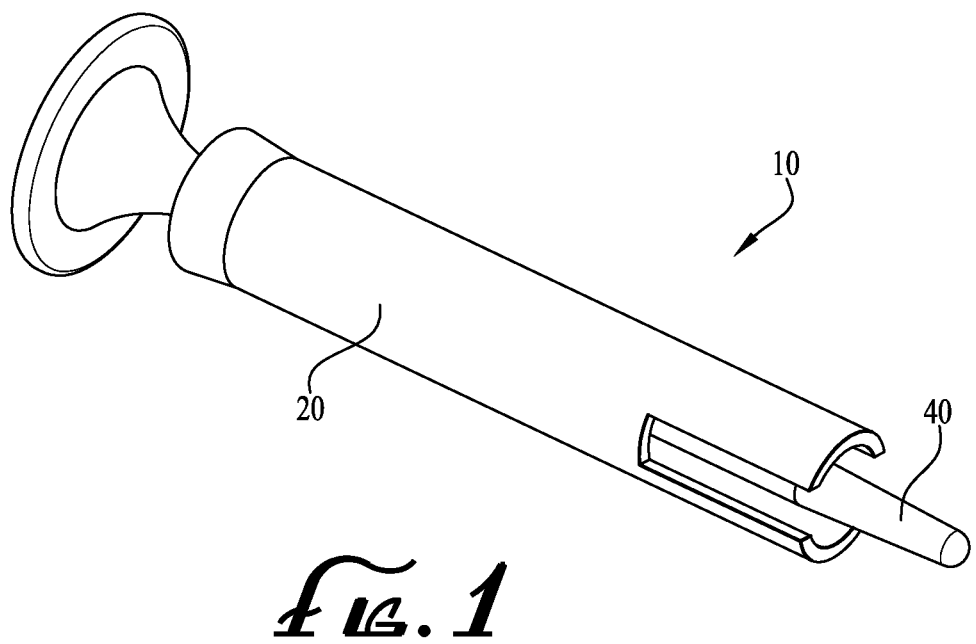
FIG. 1 shows a perspective view of an assembled cleaning device according to an example embodiment of the present invention.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, example embodiments of the invention will be described. FIGS. 1-5 show a cleaning device or swab assembly 10 according to an example embodiment of the present invention. In this embodiment, the cleaning device 10 generally comprises a swab member 20 and a guide shaft or plunger 40. The swab 20 comprises an elongate cylindrical tube member or handle 22, and extends from a first end 26 to a second end 30. In example embodiments, an opening or lumen 24 extends through the swab 20 from the first end 26 to the second end 30. As depicted in FIG. 3, the first end of the swab 20 generally includes a wall or end portion 31 formed with the swab 20 and defines the opening 24 formed generally at a central portion thereof. The second end 30 of the swab 20 generally includes at least one elongate channel 32 (in the depicted embodiment, two diametrically opposed cutout portions of the tubular body of the swab 20 define the channel 32), forming a pair of projections or swab fingers 34 at the second end 30 of the swab 20, the projections 34 being configured to extend within an outer housing of a connector (and/or within and/or through drainage openings or vents of the connector) to clean and disinfect the connector whereby any residual feeding liquids or other debris retained within the connector is removed.

The projections 34 are shown in greater detail in FIGS. 4-5. In example forms, the projections 34 comprise interior surfaces 35, exterior surfaces 37, intermediate surfaces 36, and end surfaces 38. In example embodiments, at least a portion of one or more of the surfaces 35, 36, 37, 38 are at least partially covered with a foam material, flocking, or other cleaning material CM to provide for cleaning and disinfecting at least portions of the connector during its cycle of use. The foam material CM can optionally be coated with isopropyl alcohol (ISP) or other forms of antimicrobial, antibacterial or other disinfecting/cleaning agents. In example forms, the cleaning agent comprises 70% ISP. Alternatively, other cleaning agents such as sterile water, saline, soapy water, or other agents may be utilized. The foam or other cleaning material CM is preferably compressible, absorbent and textured to facilitate a scrubbing action against portions of the connector. According to some example forms, the cleaning material CM is in the form of a brush, for example, wherein a generally rigid wire comprising a plurality of bristles extending therefrom is provided for contacting and cleaning/disinfecting the connector (as will be described below)

Referring back to FIG. 2, the plunger 40 generally comprises a rod or shaft having an actuating or gripping portion such as a flange 50 formed at a first end thereof and a plug or tip portion 52 formed at a second end thereof. The actuating portion generally comprises a gripping pad or enlarged surface area 46 and the plug portion formed at the second end of the plunger 40 is configured for insertion and sealing within a lumen of the connector (as will be described below). In example embodiments, the flange 50 is sized to be larger than the opening 24 of the swab 20 to prevent the swab from being retracted over the flange and off of the plunger.

FIGS. 6-10 show a sequence of operation of the cleaning device used to clean a connector 60 according to an example method of use of the present invention. In the depicted embodiment, the connector 60 is generally in the form of the connector disclosed in U.S. patent application Ser. No. 14/844,956, which is incorporated herein by reference and shows an improved male ENFIT connector for enteral fluid containers and vessels that includes vent or drain openings to reduce the incidence of residual feeding liquids being retained within the outer housing 70 thereof where bacterial growth or contamination might occur. The connector 60 comprises a front end, the stem 66 (comprising a lumen extending therethrough), the outer housing 70, threads 72 positioned on an internal portion of the outer housing 70 (see FIG. 16A), a pair of vent openings 174 (see FIG. 12), a cap 80, a tether 82 attaching the cap 80 to the connector 60, a handle 83 for gripping the cap 80, a body 84, and a seal plug 86.

Figure 6:
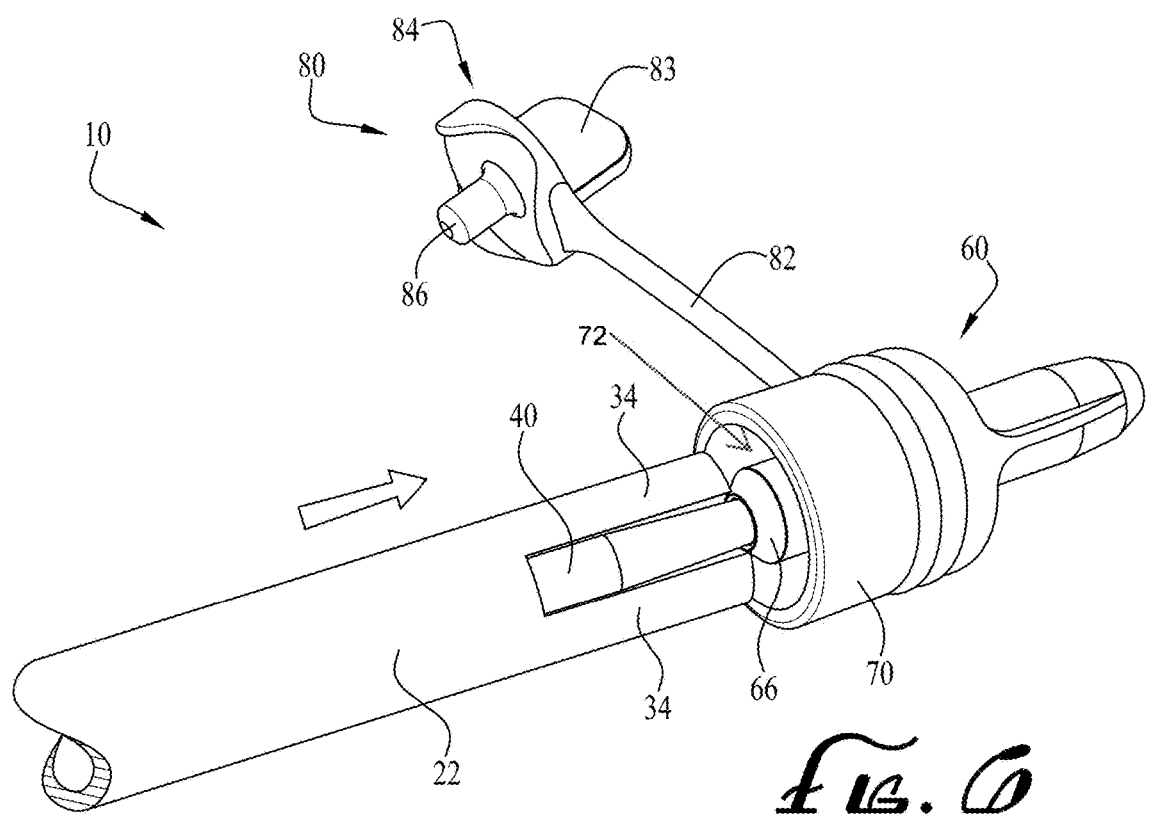
FIGS. 6-10 show a sequence of operation using the cleaning device of FIG. 1 to clean a connector, according to an example method of the present invention.

As shown in FIG. 6, the swab 20 is mounted over the plunger 40 with the plug end 52 of the plunger projecting outwardly from the second end 30 of the swab 20. The plug 52 is removably inserted into the lumen of the male connector stem 66 of the connector 60 to seal the lumen extending through the stem 66. According to example forms, the plug sealingly engaging the lumen preferably prevents contamination of the lumen from debris or the cleaning agent during the cleaning process (as will be described below). In example forms, a user's thumb or finger may press against the pad 46 and/or flange 50 to force the plug 52 to removably and sealingly engage the lumen. According to some example forms, the plug 52 is generally sized and shaped similarly to the seal plug 86 of the cap 80.

Figure 7:
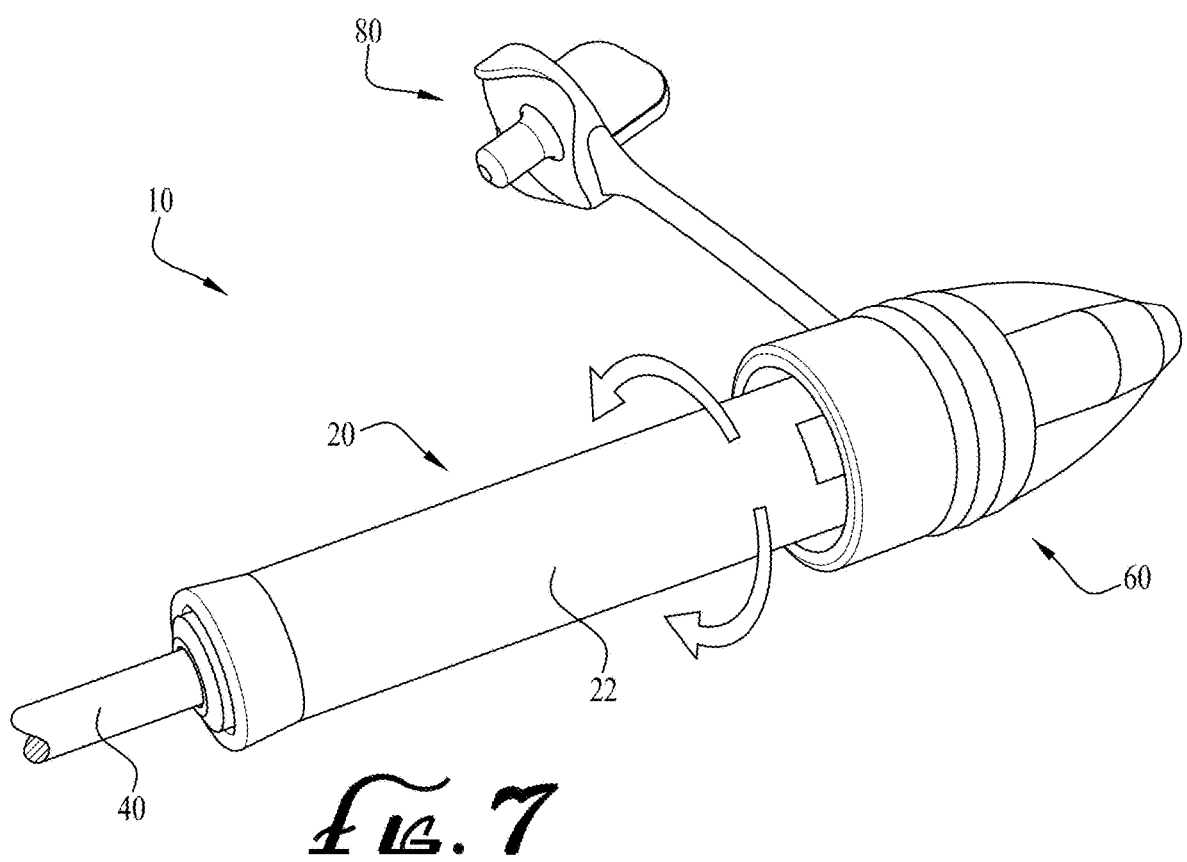
Figure 8:
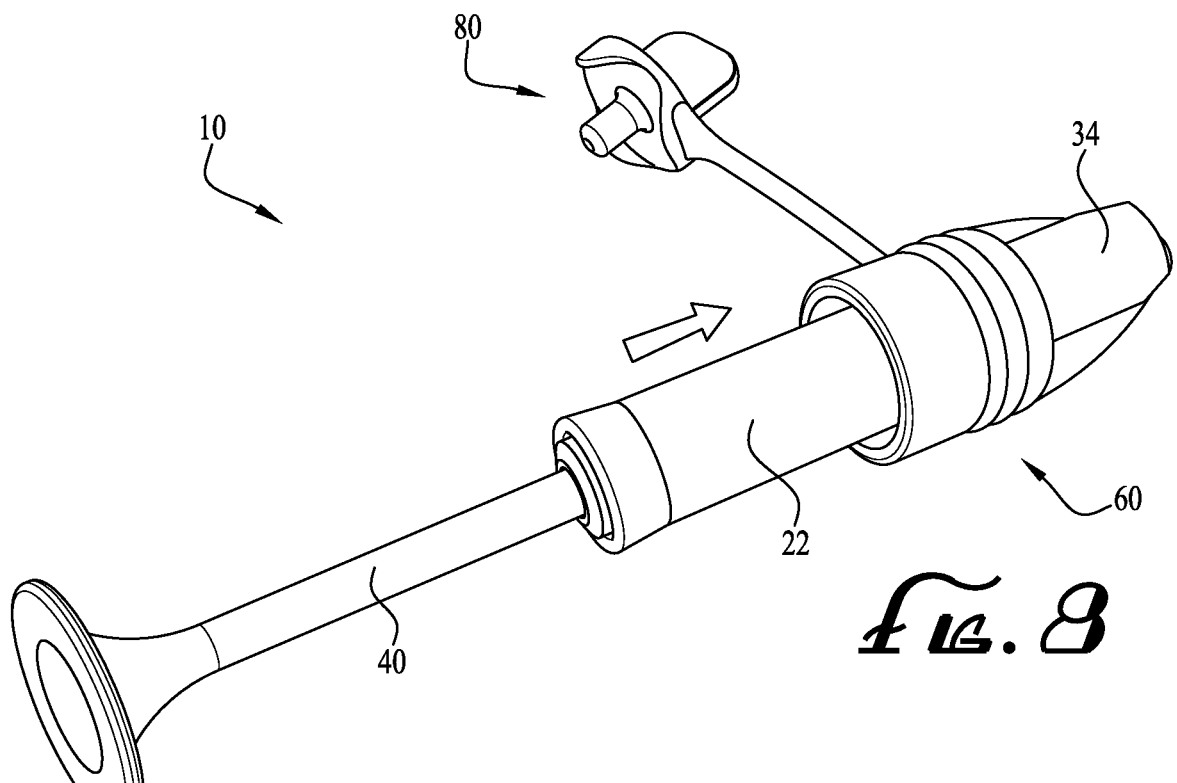

Once the plug is inserted and sealed within the lumen of the connector stem 66, the swab 20 is advanced in a traversing or translational movement along the plunger 40 such that the projections 34 begin to move between the outer housing 70 and the connector stem 66. As shown in FIG. 7, the projections 34 are generally positioned between the outer housing 70 and the stem 66 so that the swab 20 is capable of rotation about the plunger 40, thereby allowing the projections 34 to rotationally move therebetween to clean and/or disinfect (e.g., removing any feeding fluids or other debris and potential contaminants that may be contained therein). Next, as shown in FIG. 8, the swab 20 is further advanced along the plunger 40 such that the projections 34 extend through the vent openings 174 of the connector 60 to further clean and/or disinfect the connector and remove any feeding fluid or residue present due to fluid drainage through the vent openings 174. Thus, by having the plug sealingly engaged with the lumen of the stem 66, debris and/or the cleaning agent of the projections 34 (or foam material CM thereof) are prevented from being introduced into the lumen when cleaning (e.g., translational and/or rotational motion of the swab 20 whereby the projections 34 are generally positioned between the outer housing 70 and the connector stem 66).

Figure 9:
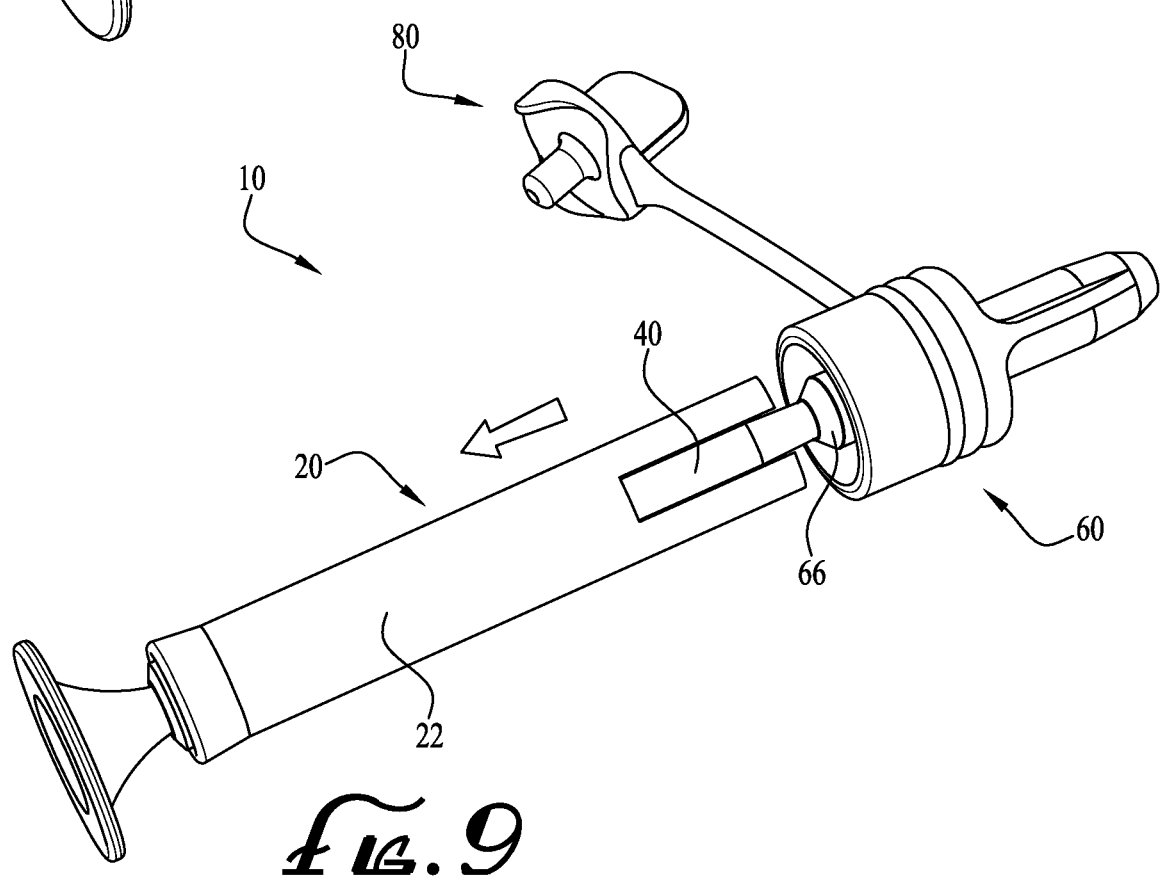
Figure 10:
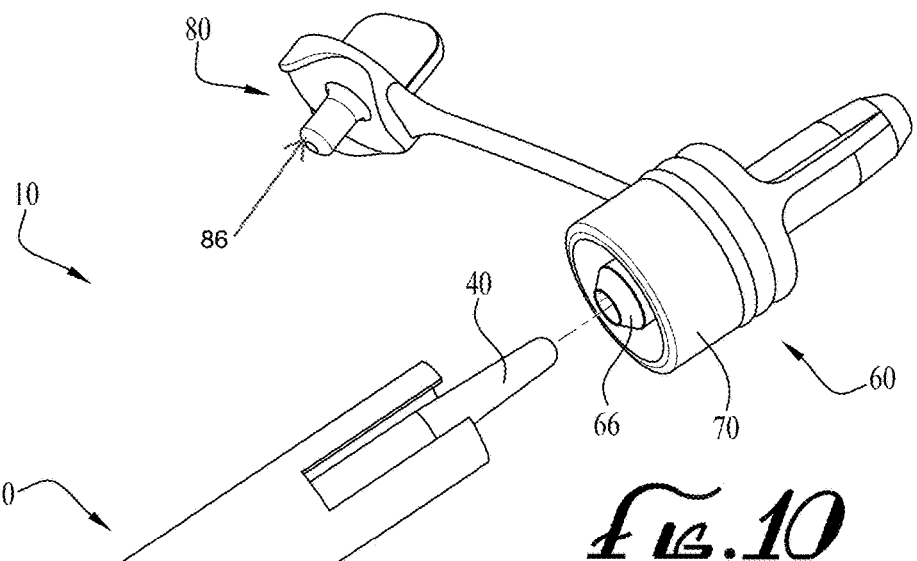
Figure 11:
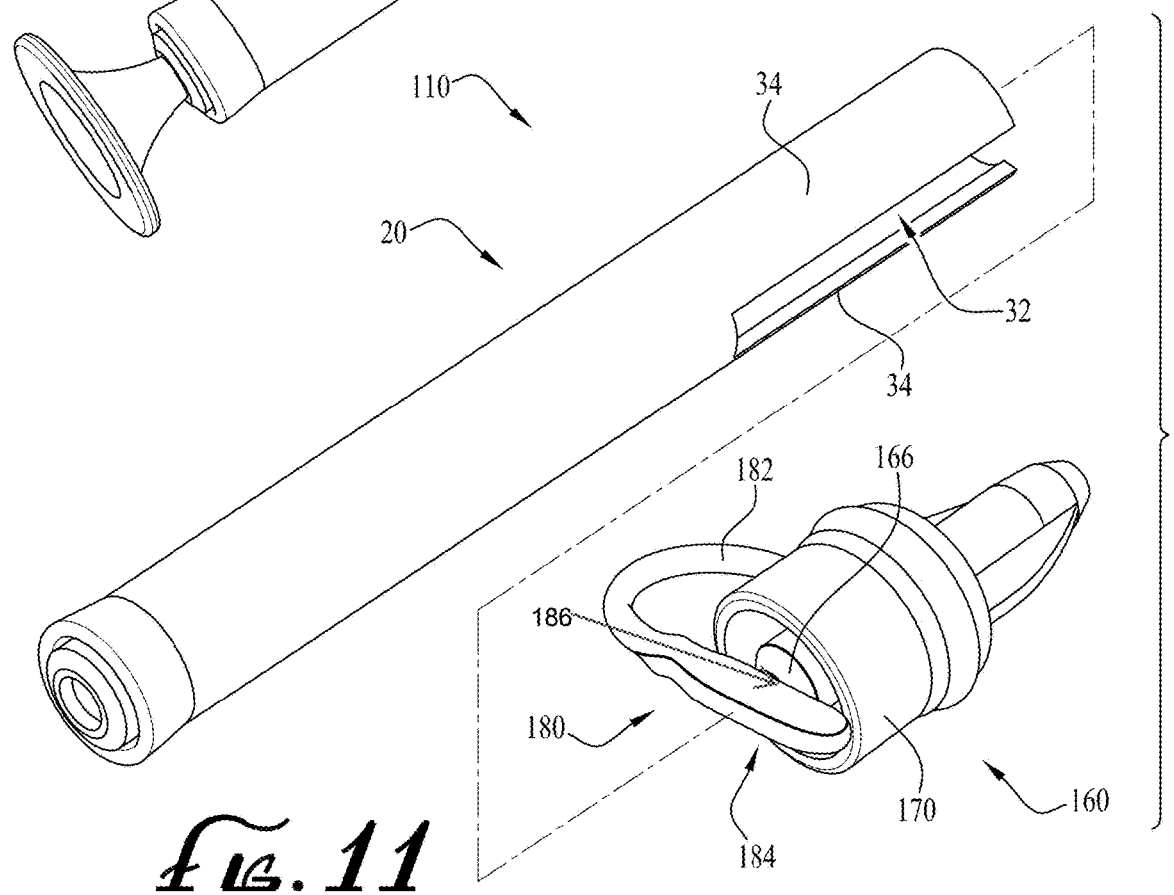
FIG. 11 shows a cleaning device according to another example embodiment of the present invention, and a connector with which the cleaning device may be utilized.

As shown in FIG. 9, the swab 20 can then be retracted rearward, causing the projections 34 to be withdrawn from the vent openings 174 and from between the stem 66 and outer housing 70. The plug end 52 of the plunger 40 preferably remains inserted in the lumen of the connector stem 66 while the swab 20 is withdrawn from the connector 60 to prevent contamination that may be present on the swab 20 from entering the lumen of the connector stem. After the swab is withdrawn, the plug 52 is disengaged from the lumen of the connector stem 66 as shown in FIG. 10. In example forms, traversing the swab 20 along the plunger 40 is generally carried out by grasping a portion of the tube 22, and engaging and disengaging the plug 52 to/from the lumen of the connector stem 66 is carried out by pressing or pulling on the actuating end of the plunger 40 (e.g., the pad 46 and/or flange 50). After the plug 52 is disengaged from the lumen of the connector stem 66, the seal plug 86 of the cap 80 can then be inserted into the lumen of the connector stem 66 so that further contamination therein is prevented.

Optionally, according to additional example embodiments of the present invention, the channel 32 of the swab 20 can be configured to follow a generally helical path such that the pair of projections 34 generally follow a helical path, for example, instead of the projections 34 being generally linear as depicted. In this manner, the projections 34 can still be positioned between the outer housing 70 and the stem 66 so that the swab 20 is capable of rotation about the plunger 40, thereby allowing the projections 34 to rotationally move therebetween to clean and/or disinfect (e.g., removing any feeding fluids or other debris and potential contaminants that may be contained therein). Furthermore, when the swab 20 is further advanced along the plunger 40 such that the projections 34 extend through the vent openings 174, the swab 20 is rotated (and translated) to cause greater or less engagement with the vent openings 174, for example, since the channel 32 follows a helical path. Thus, in example forms, rotational movement can be provided for cleaning of the connector when the projections 34 are positioned between the outer housing 70 and the stem 66 and when the projections 34 move through the vent openings 174.

Figure 12:
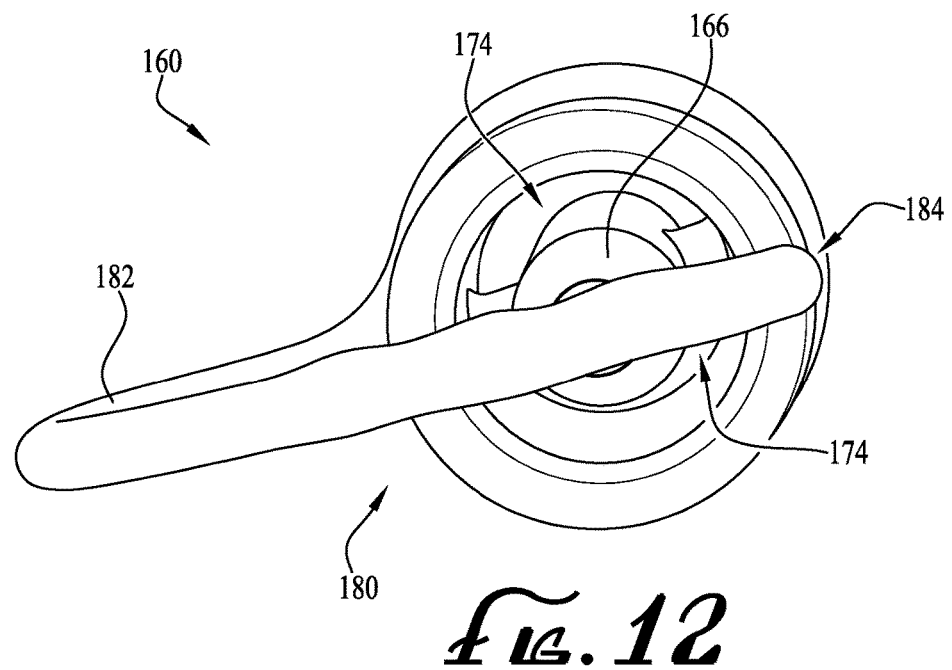
FIG. 12 shows an end view of the connector of FIG. 11.
Figure 13:
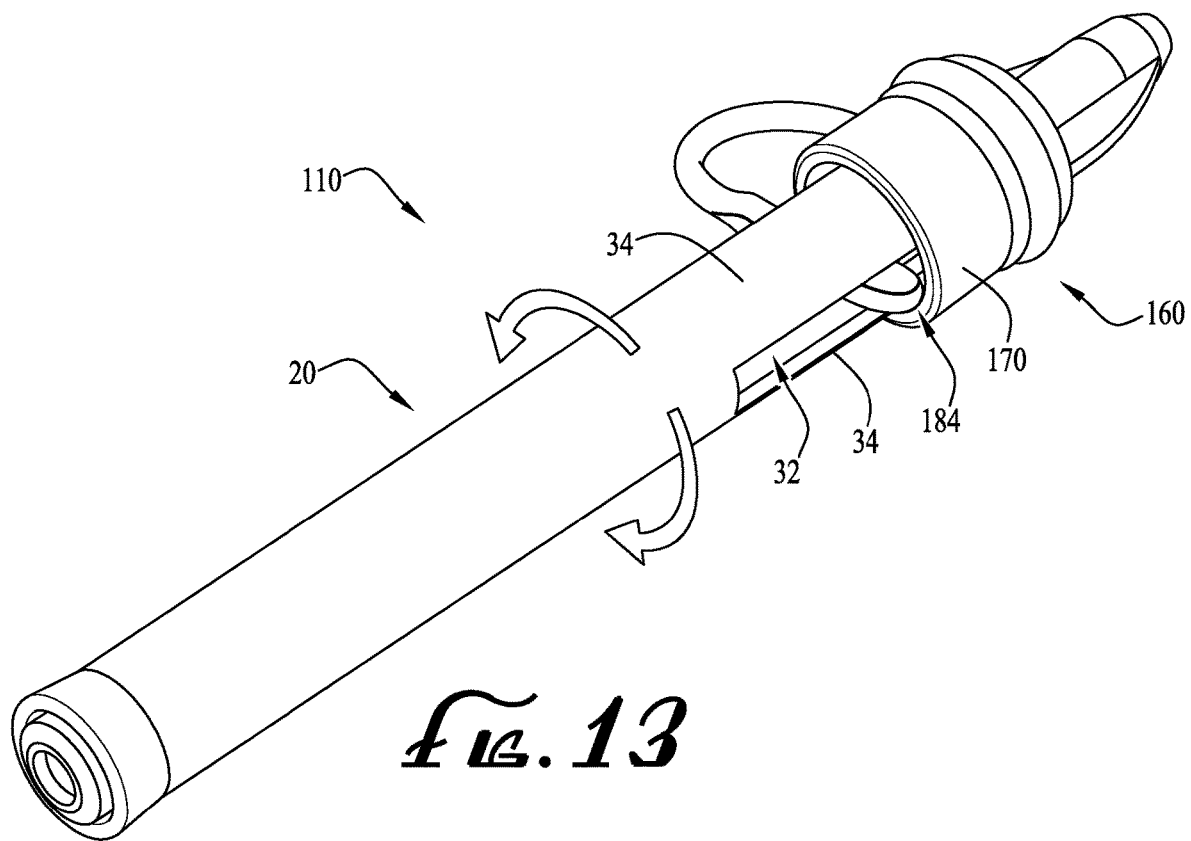
FIGS. 13-14 show a sequence of operation using the cleaning device of FIG. 11 to clean the connector, according to another example method of the present invention.
Figure 14:
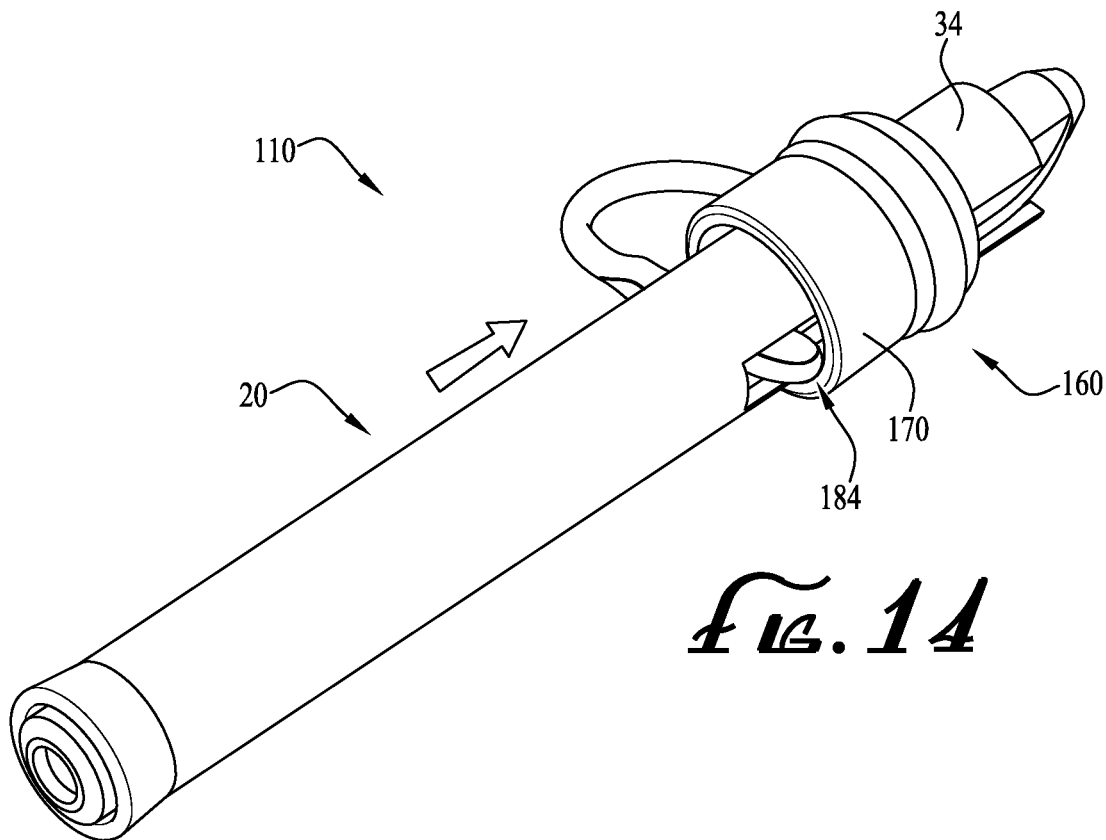

FIGS. 11-14 show a cleaning device or swab assembly 110 comprising a swab 20 substantially as described above, and a modified coupling or connector 160 according to another example embodiment of the present invention. The connector 160 comprises a cap 180 comprising a generally flanged or rib-like body 184 and a seal plug 186 extending therefrom (shown as being fully inserted within the lumen of the stem 166). In example embodiments, a tether 182 optionally connects the cap 180 to the connector 160, as similarly described above. Preferably, rather than providing a plunger for sealing the lumen of the connector stem 166, the seal plug 186 is utilized to seal the lumen while also allowing the projections 34 of the swab 20 to be inserted between the outer housing 170 and the stem 166. As depicted in FIG. 12, the rib-like body 184 of the cap 180 is preferably configured, sized and shaped to fit within the channel 32 of the swab 20 and to allow the projections 34 to extend within the connector, between the outer housing 170 and the stem 166 (see FIG. 13), and within and through the vent openings 174 (see FIG. 14). Preferably, as shown in FIG. 13, when the projections 34 are inserted within the connector 160 (between the outer housing 170 and the stem 166), the body 184 of the cap 180 is received within the channel 32. In an example manner of use, the seal plug 186 remains sealingly engaged with the lumen of the stem 166, and the swab 20 can be rotated to clean within the housing and vent openings, which causes the plug 180 and tether 182 to rotate therewith. As depicted in FIG. 14, the swab 20 can be further advanced within the connector 160 such that the projections 34 extend through the vent openings 174. In example forms, since the seal plug 186 is plugging the lumen rather than the plunger 40 as described above, the channel 32 of the swab may be sized accordingly (e.g., width, length, etc.) to provide for fitting around the body 184 and permitting adequate extension of the projections 34 through the vent openings 174.

Figure 15:
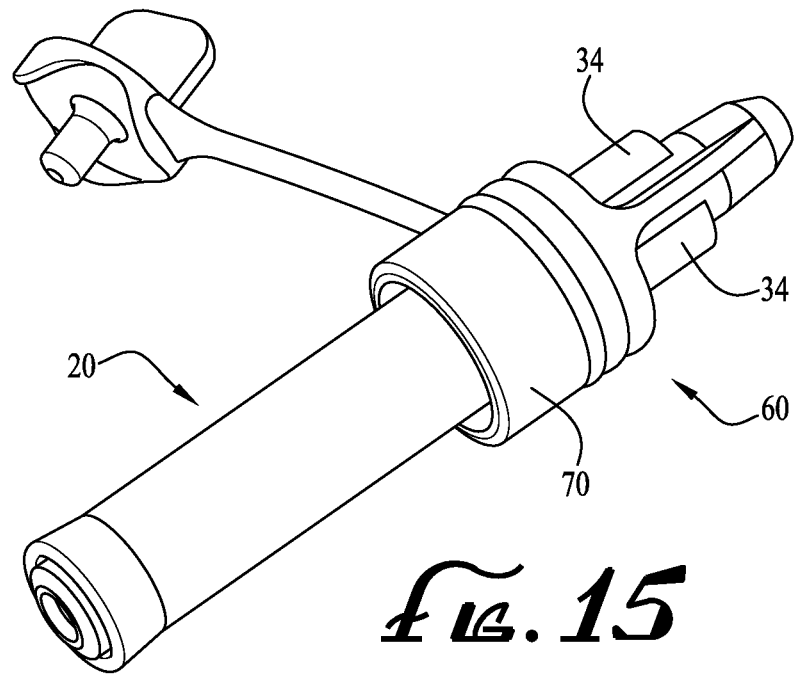
FIG. 15 shows a cleaning device engaged with a portion of a connector, according to another example embodiment of the present invention.

FIG. 15 shows another method of use of the swab 20 to clean a connector 60 according to the present invention. As depicted, the swab 20 is applied for cleaning the connector 60 without the use of the plunger 40 or seal plug 86 to seal the lumen of the connector stem 66, for example when the risk of debris entering the lumen of the connector stem is small or is not of concern (e.g., a final wipe-down to remove residual fluid after use of the connector is complete, prior to disposal).

FIGS. 16-22 show a cleaning device 210 according to another example embodiment of the present invention. As depicted, the cleaning device 210 generally comprises a housing 212, at least one brush member 230 mounted to the housing 212, and a guide shaft or plunger 240. According to one example form, the housing 212 comprises a first housing half or shell 214 and a second housing half or shell 216, wherein the housing shells 214, 216 are generally similarly sized and shaped about an axis of symmetry, and whereby one or more snap fittings, crush pins, connectors or other coupling features thereof provide for joining the two shells 214, 216 together to form the housing 212. According to example forms, the housing 212 is generally cylindrical in shape and comprises a first end having a generally recessed area for receiving a portion of the plunger 240 (as will be described below) and a second end comprising a pair of generally elongate and oppositely-positioned flanges 224 defining an enlarged orifice 221 within the housing 212. According to example forms, the plug 252 of the plunger 240 is configured to be engaged with the lumen of the connector to be cleaned, and the housing 212 and brushes 230 attached thereto are configured to move along the plunger 240 so that the brushes can move within the outer housing and along an exterior of the stem of the connector so that the brushes 230 are capable of rotation about the plunger 240, thereby allowing the brushes 230 to rotationally move therebetween (e.g., between an outer portion of the stem and against an interior wall of the outer housing of the connector) to clean and/or disinfect (e.g., removing any feeding fluids or other debris and potential contaminants that may be contained therein).

Figure 19:
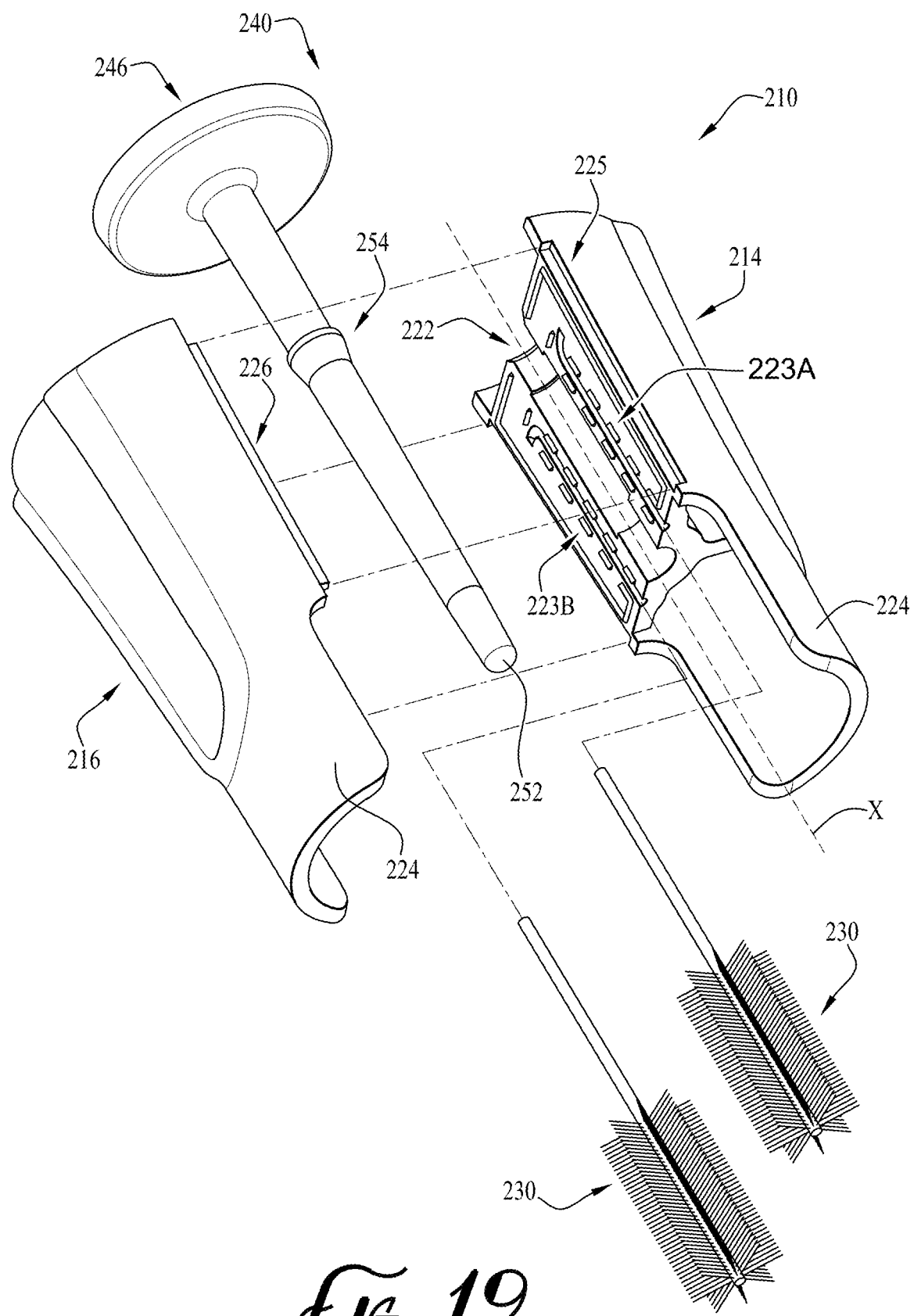
FIG. 19 shows a front perspective assembly view of the cleaning device of FIG. 16.
Figure 20:
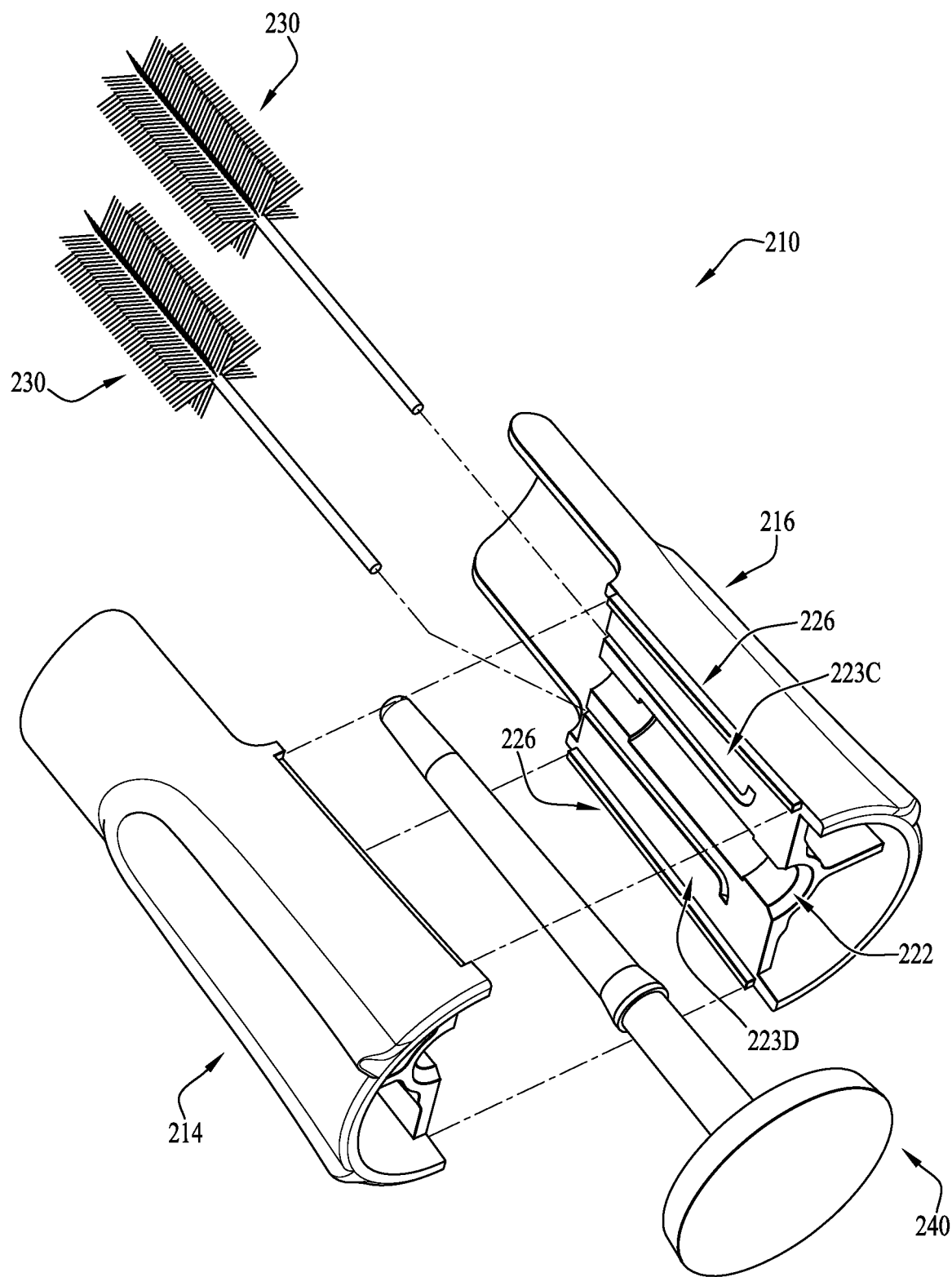
FIG. 20 shows a rear perspective assembly view of the cleaning device of FIG. 19.
Figure 24:
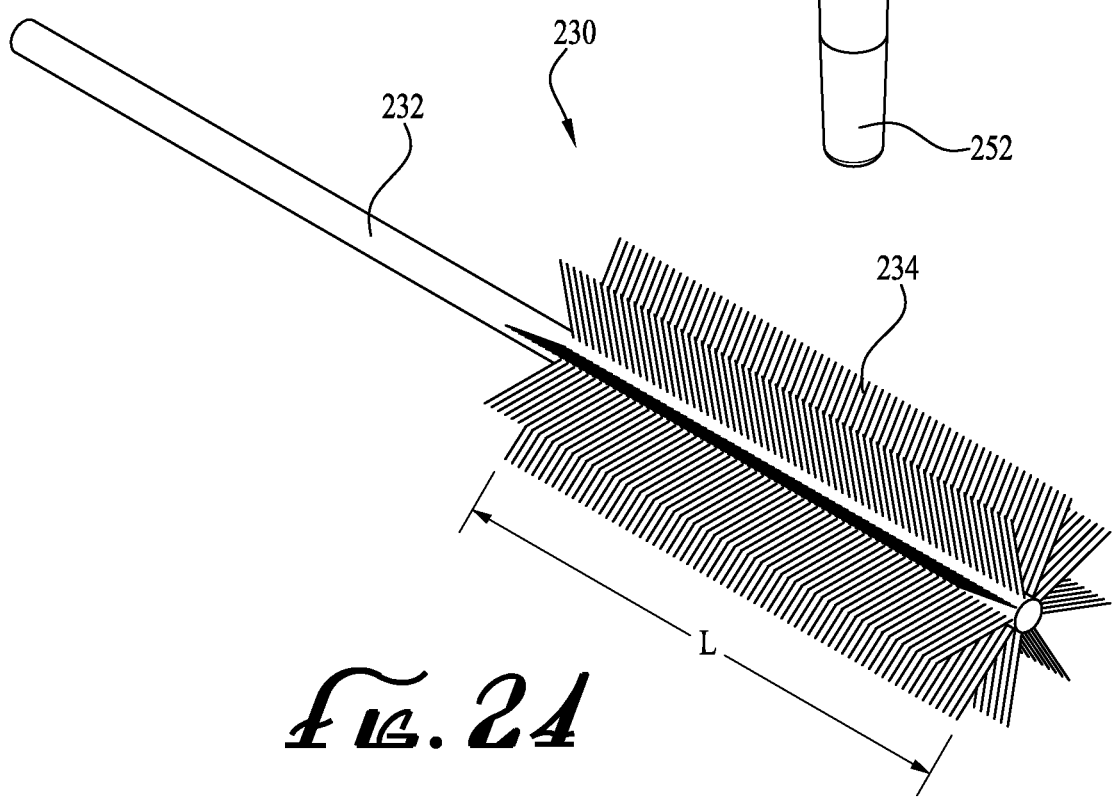
FIG. 24 shows a perspective view of a brush member of the cleaning device of FIG. 16.

As depicted in FIGS. 19-22, the shells 214, 216 comprise generally elongate channels 223A-D for receiving a rod portion 232 of the brushes 230 (see FIG. 24). According to example forms, the channels 223A-D are generally parallel and laterally offset a small distance from a central channel 222 defining a longitudinal central axis X that generally extends between the ends of the housing 212, for example, which provides for capturing a retaining feature 254 of the plunger 240, for example, to permit translation of the plunger 240 relative to the housing 212, and to also permit rotation of the housing 212 relative to the plunger 240. Preferably, the shells 214, 216 comprise one or more coupling features for providing engagement therebetween, for example, to form the housing 212. According to one example form, the coupling features are in the form of female projection elements 225 formed in the first housing shell 214 and male projection elements 226 formed in the second housing shell 216. As depicted in FIGS. 19-20, the coupling elements 225, 226 are generally positioned along at least a majority of the length of the housing (near the outer periphery thereof), and provide a snap fit engagement together, for example, to provide a generally elongate, cylindrical housing member 212. One of ordinary skill in the art will appreciate that the housing shells 214, 216 can couple together in a plurality of different formats and can comprise a plurality of different engagement features. Alternatively, the housing 212 is generally formed from one integrally formed, unitary member, for example, rather than two separate half-shell pieces. In further alterative embodiments, the outer housing shells are generally hingedly connected together, for example, such that the shells are capable of pivoting relative to each other between an open configuration and a closed, snapped-together configuration.

Figure 16:
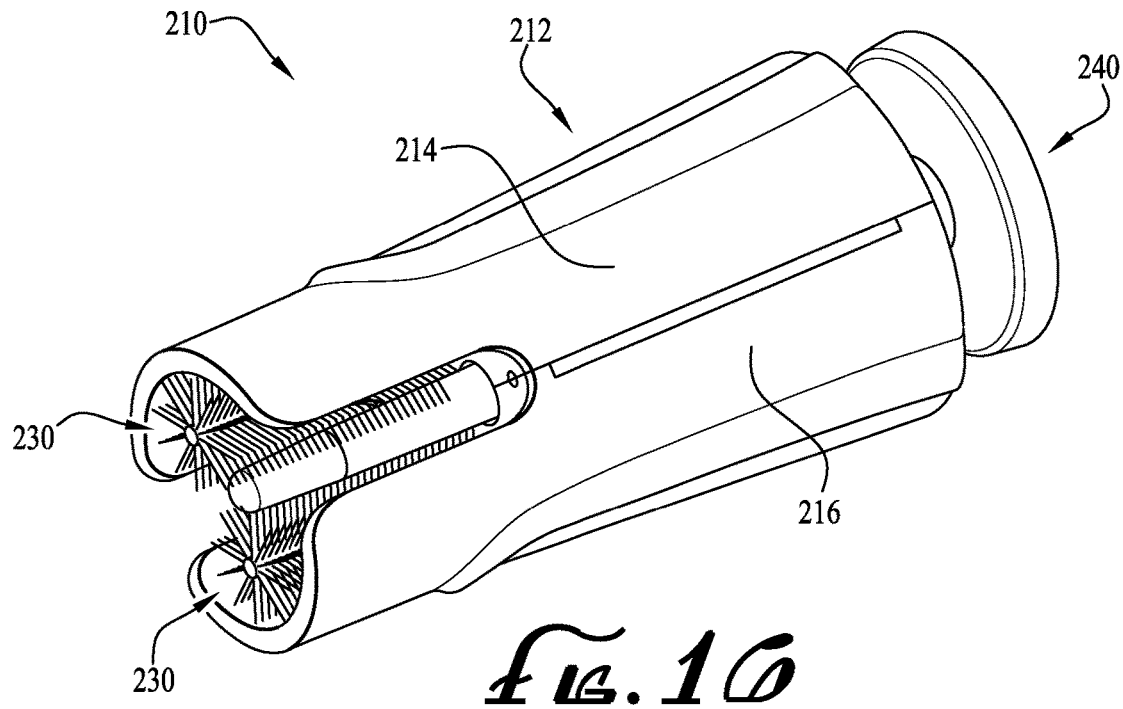
FIG. 16 shows a front perspective view of a cleaning device according to another example embodiment of the present invention, showing the plunger thereof in a retracted state.
Figure 17:
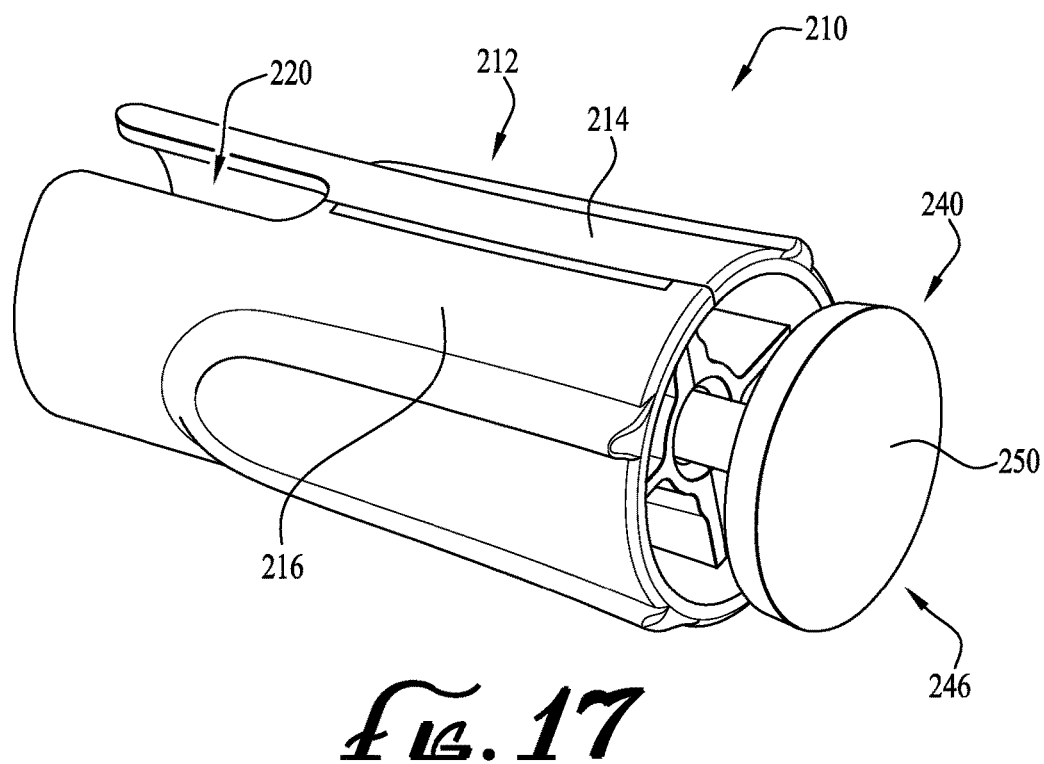
FIG. 17 shows a rear perspective view of the cleaning device of FIG. 16.
Figure 18:
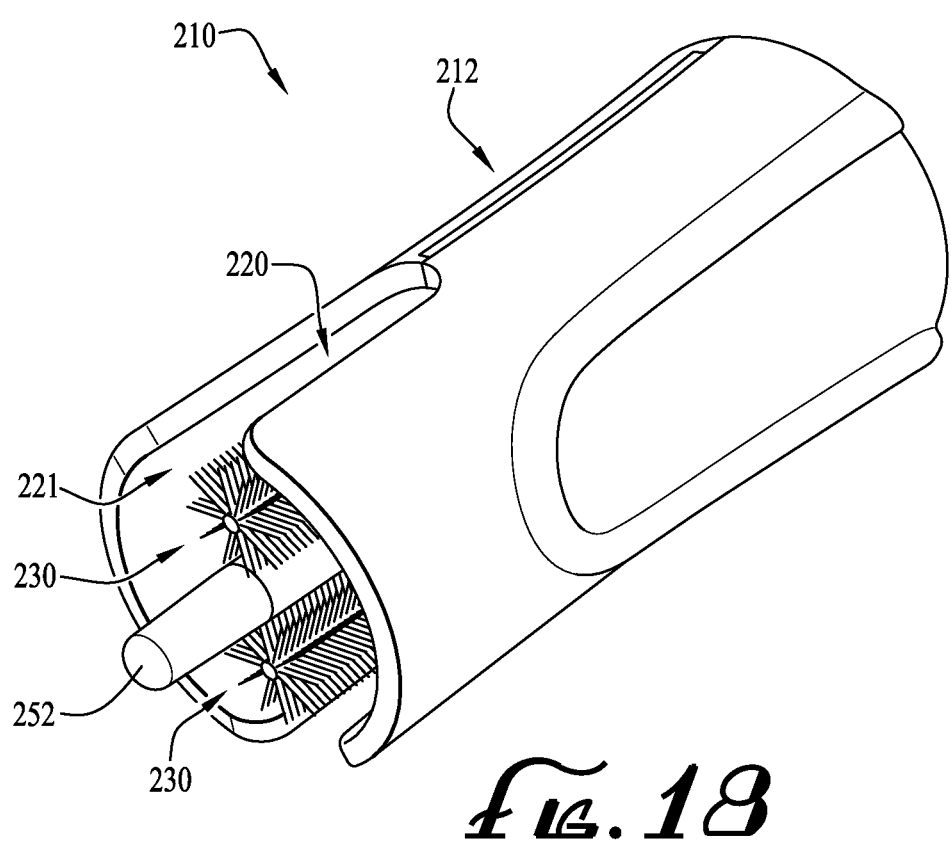
FIG. 18 shows a front perspective view of the cleaning device of FIG. 16, showing the plunger in the extended state.
Figure 21:
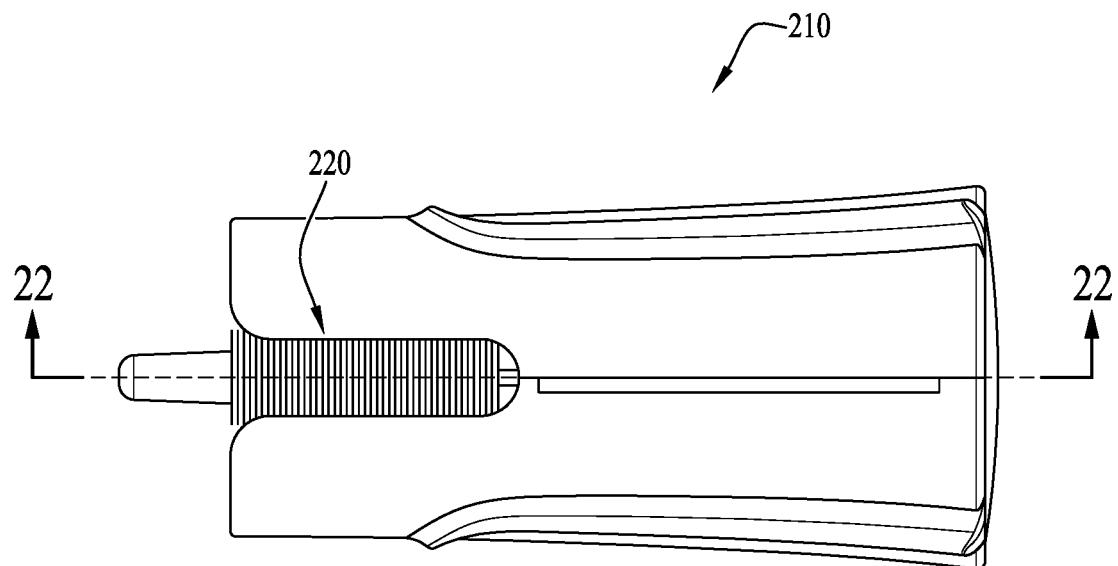
FIG. 21 shows a side view of the cleaning device of FIG. 18.
Figure 22:
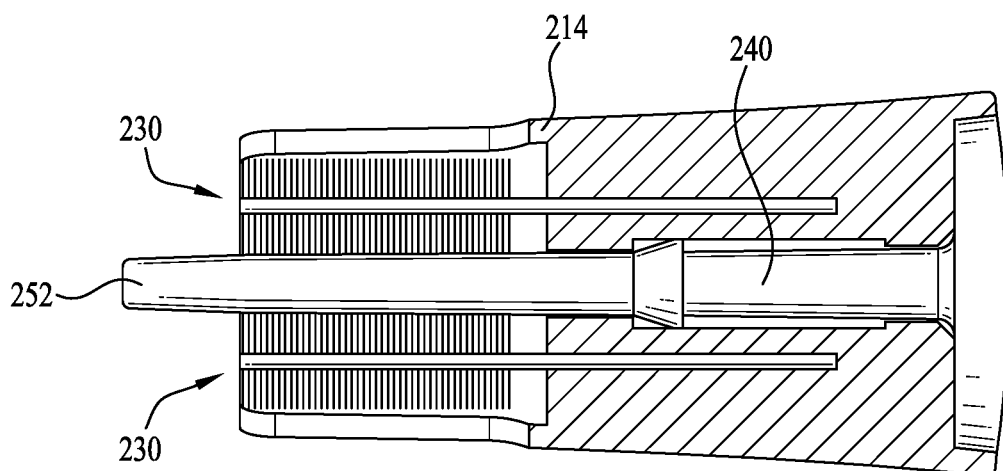
FIG. 22 shows a cross sectional view of the cleaning device of FIG. 21 taken along line 22-22.
Figure 23:
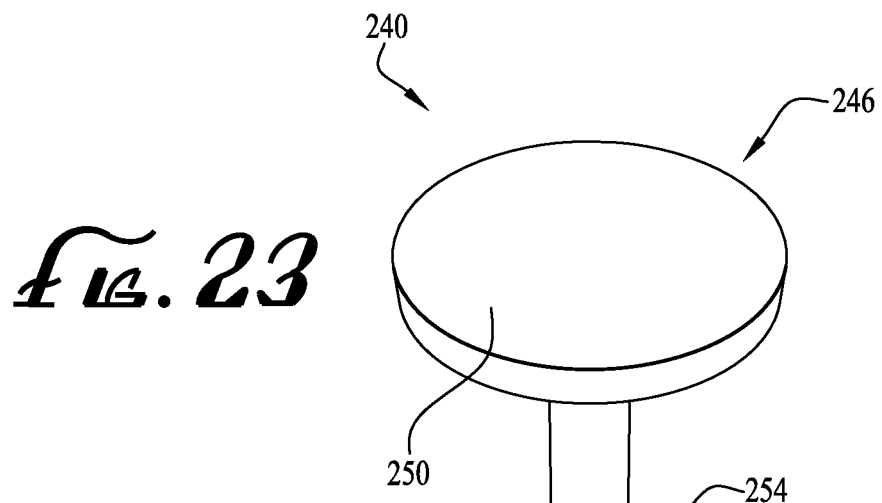
FIG. 23 shows a perspective view of the plunger of the cleaning device of FIG. 16.

As depicted in FIGS. 16-17, the plug 252 of the plunger 240 is generally in a retracted state within a portion of the housing and generally adjacent the flanges 224. In the retracted state, the plug 252 is generally intended to be engaged with the lumen of the connector such that the brushes 230 (generally laterally offset or spaced outwardly relative to the plug 252) can fully extend between the stem and the outer housing of the connector. As depicted in FIGS. 18 and 21-22, the plunger 240 is in the extended state wherein the plug 252 extends beyond the ends of the flanges 224. Generally described, the actuating portion, gripping pad or end portion 246 (comprising the flange 250) is generally fitted within the recessed area of the first end of the housing 212. Generally, when the cleaning device is not in use, the plug 252 remains in the extended state—projecting outwardly from the second end of the housing 212 beyond the flanges 224. In example forms, the flanges 224 are sized and shaped such that generally elongate, diametrically opposed channels 220 are defined along a portion of the housing, for example, generally starting at the second end of the housing 212 and extending towards the first end. In example forms, the channels provide access to the orifice 221 of the housing 212, for example, where the brushes 230 are positioned. As will be described below, the channels preferably provide for the application of a cleaning agent to the brushes 230 when the plug 252 is engaged with the lumen of the connector.

The plunger 240 generally comprises the end portion 246 having the flange 250 and a plug 252 at an end generally opposite the end portion 246 for engaging the lumen. The retaining feature 254 is generally positioned on a portion of the plunger 240 between the ends. Generally, the retention feature 254 is an outwardly-extending, skirt-like projection, which is preferably sized and shaped to movably mount within the central channel 222 of the housing 212. Preferably, the retention feature 254 is sized and shaped such that the plunger 240 is capable of translational and rotational movement relative to the housing 212, for example, to allow the housing 212 and brushes fixed relative to the housing 212 to move along the plunger rod once the plug 252 is engaged with the lumen of the connector. However, the retention feature 254 prevents the plunger 240 from becoming disengaged from the housing 212.

In example forms, each brush 230 generally comprises an elongate rod 232, whereby at least a portion of the rod 232 comprises a circular array of bristles 234 extending therefrom. According to example forms, the brush 230 comprises a circular array of about nine (9) linear arrays of bristles 234. According to one form, the length of each linear array of bristles 234 is generally between about 4-25 millimeters, for example between about 8-20 millimeters, and in a particular example about 14 millimeters. The entire length of the brush 230 is generally between about 10-50 millimeters, for example between about 20-40 millimeters, and in a particular example about 30.8 millimeters. According to example forms, the length of each bristle 234 is generally between about 1-5 millimeters, for example between about 2-4 millimeters, and in a particular example about 2.35 millimeters. According to example forms, the bristles 234 may be formed from any desired material. According to one example form, the bristles 234 are formed from a nylon filament, for example, DuPont Tynex® 612 nylon filament.

In use, the cleaning device 210 is provided for cleaning and disinfecting the area of the connector between the stem and outer housing portion. With the plunger in the extended state, the plug 252 is engaged with the lumen of the connector, and then the housing (and brushes 230 affixed thereto) are permitted to move along the length of the plunger 240 such that the bristles 234 extend within the connector between the stem and outer housing thereof. This causes the plunger 240 to be moved to the retracted state wherein the plug 252 is generally recessed within housing 212 near the second end (see FIGS. 16-17). In example forms, the flanges 224 of the housing are generally sized and shaped to permit the outer housing of the connector to be fitted therein, and wherein the brushes 230 (generally laterally offset from the flanges 224 and plug 252) are appropriately positioned to fit between the stem and an internal surface or wall of the outer housing of the connector. The housing 212 is then rotated around the plunger 240 (with the plug 252 engaged with the lumen) to clean and disinfect the connector. Once the cleaning and disinfecting of the connector has been performed, the user can disengage the cleaning device 210 from the connector by grasping the housing 212 and pulling away from the connector. Optionally, once the plug 252 of the plunger 240 is engaged with the lumen, and prior to the housing and brushes moving along the plunger 240 to clean and disinfect the connector, a cleaning agent can be applied to the bristles 234 of the brushes 230 through the channels 220. Thus, the cleaning device is configured such that a cleaning agent can be applied to the brushes 230 while in the connected state with the lumen of the stem.

In alternate embodiments, one, two, or more brushes can be mounted to the housing 212. Furthermore, the length of the brushes 230 and the bristles 234 may be longer or shorter in alternate embodiments. According to some example forms, multiple brushes having different brush lengths and bristle lengths may be provided for interchangeable or replaceable installation in the housing 212. Further optionally, the brushes may be mounted to the housing 212 by various different coupling means. For example, the brushes may be integrally formed with the housing 212 or formed with the housing 212 (or shells thereof) during the molding process, for example, by over molding.

FIGS. 25A-26 show further details of a connector 360 according to example embodiments to which the cleaning swab devices (including brushes) and methods of the present invention may be applied, as described above. In example forms, the connector 360 is generally in the form of a male ENFit connector according to ISO 80369 standards, which comprises a stem 366 (comprising a lumen extending therethrough), an outer housing 370, and threads 372 formed on an internal portion of the outer housing 370. Generally, a tube T is coupled to a rear end portion thereof (and in communication with the lumen of the stem 366), which provides a conduit or path through which the feeding fluids flow. According to example forms, the connector 360 may be generally sized and shaped similarly to the connector 60 as described above. In one example embodiment, a swab 20 as shown above is used with or without a plunger 40 in similar fashion to the above described methods to clean the connector 360. According to another example form, a swab 20 without the elongate channel 32 (see dashed lines of FIG. 2 depicting the end of the tube 22 without the elongate channel 32) can be used with the connectors 60, 160, 360 to clean and disinfect the same, particularly when the connector does not include drainage or vent openings.

According to another example embodiment, the present invention relates to a method of cleaning and/or disinfecting a connector. As described above, the connector comprises a stem having a lumen extending therethrough, an outer housing, and threads positioned on an internal portion of the outer housing. The method comprises providing a cleaning device comprising a generally elongate cylindrical swab member comprising a first end and a second end, the first end generally opposite the second end, and an opening defined within the cylindrical member and extending from the first end to the second end; engaging an end of the swab with the connector, the end of the swab generally being positioned between the stem and the threads of the connector; translating and/or rotating the swab relative to the connector while the end of the swab is engaged with the connector; and disengaging the swab from the connector.

Figure 27:
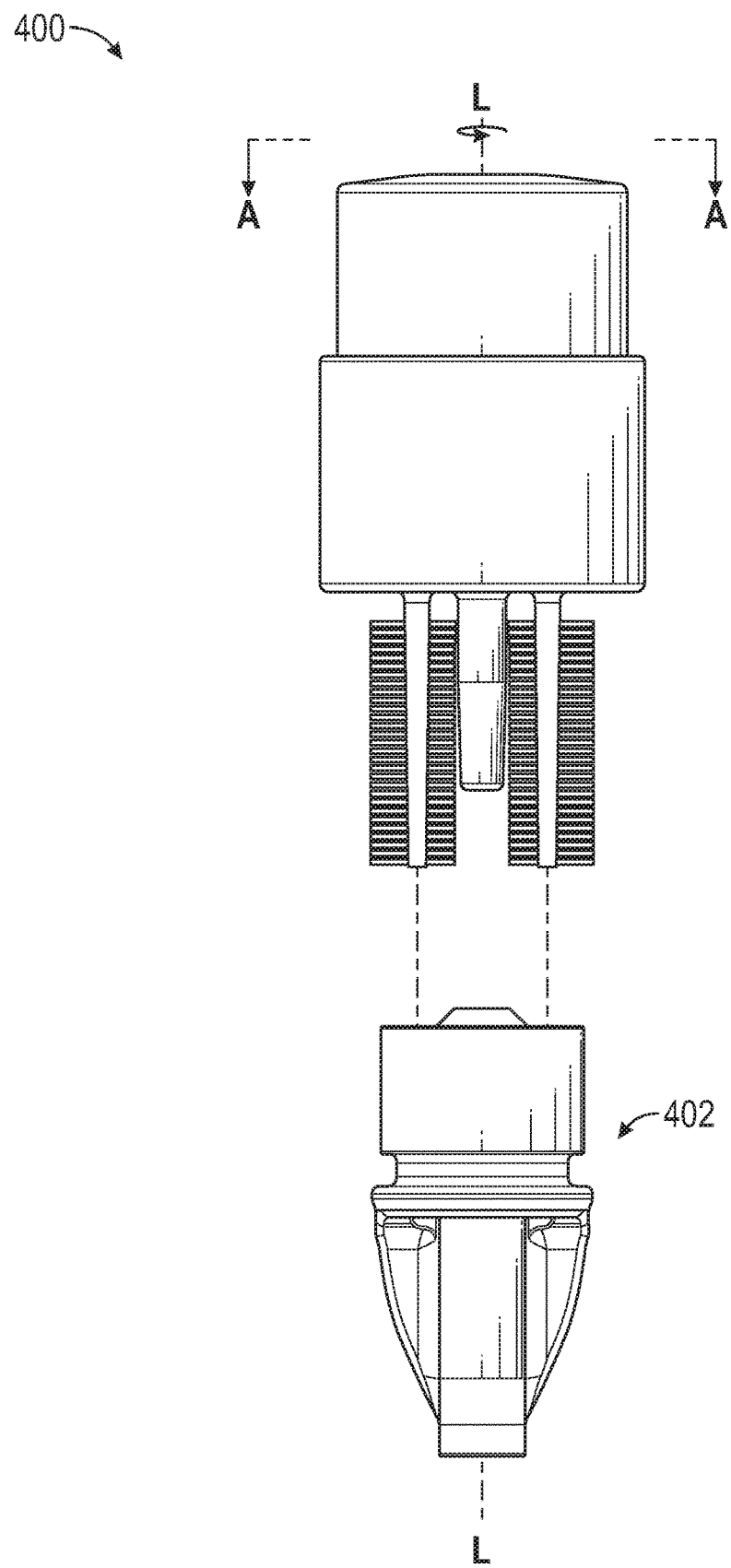
FIG. 27 is a plan view of a cleaning device for cleaning a connector, according to another example embodiment of the present invention, showing a schematic diagram of the cleaning tool disconnected from a connector to be cleaned.
Figure 28:
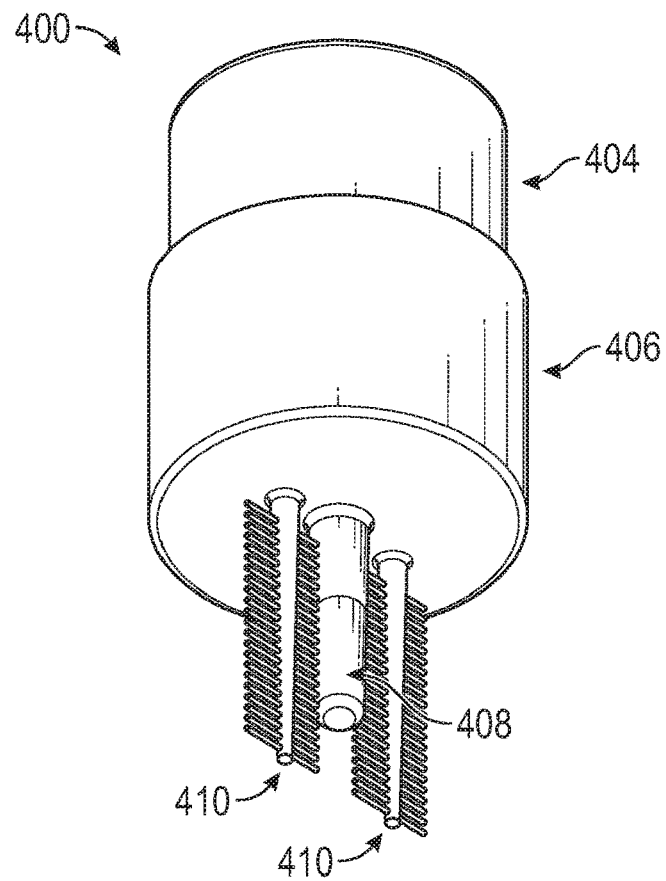
FIG. 28 is a perspective view of the cleaning end of the cleaning device shown in FIG. 27.

FIGS. 27-32 represent general concepts relating to a cleaning device 400 according to another example embodiment of the present invention. In example embodiments, the cleaning device 400 is preferably disposable and easily manufacturable without requiring much assembly. FIG. 27 specifically illustrates the cleaning device 400 in separated alignment with a connector 402 to be cleaned. The illustrated connector 402 can be similar in structure and function to the connectors described above, for example an ISO 80369-3 compliant ENFit connector. In use, the cleaning device 400 can be inserted into and rotate about a connection axis L with respect to the connector 402.

As more specifically illustrated in FIGS. 28-32, the cleaning device 400 generally comprises an elongate body extending from a first end to a second end and comprises a first plug component (or plunger member) 404 and a second cleaning component (or brush member) 406. In example embodiments, the plunger member 404 and brush member 406 are generally formed separately and configured for interengagement therebetween, for example, wherein the plunger member is generally movable relative to the brush member.

The illustrated plunger member 404 comprises an elongate plunger rod 408 that is generally centrally positioned and extending from a fixed end 414 at a collar or cap-like member 418 to a distal free or plug end 416. The brush member 406 comprises a collar member comprising a central opening 412 for receiving the plunger 408 (and permitting the plunger to translate and rotate therethrough), and a pair of brushes 412 (or cleaning swabs) extending from the collar member.

In example embodiments, at least a portion of the plunger 408 comprises an outer flange or tab 426 that is configured for engagement with the central opening 412 of the collar member of the brush member 406, together forming a locking or support assembly ensuring that the plug member 404 and the brush member do not become easily disconnected once they are connected as illustrated. As illustrated, the tab 426 of the plug member 404 can have a tapering ramp-geometry which allows for insertion through the central opening 412. The tab 426 can extend circumferentially around the outer surface of the plunger 408. The central opening 412 is sized such that, once inserted therethrough, the outer flange 426 is prevented from passing therethrough, for example, such that the two members (i.e., plunger member 404 and brush member 406) are substantially prevented from freely disconnecting after being assembled together.

In the illustrated embodiment, each brush 410 comprises an elongate rod 420 comprising a plurality of substantially smaller projections or rods 422, 422 (or bristles) generally extending therefrom in opposing pairs, for example, wherein they extend generally perpendicular to the extension of the elongate rod. The elongate rods 420 extend generally parallel to the connection or cleaning axis L. In example embodiments, the brushes 410 are integrally formed with the brush member 406, for example, wherein a single mold forms the entirety of the brush member, for example, the collar member and the pair of brushes. In some example embodiments, only one brush 410 is provided. In other example embodiments, two or more brushes can be provided. The illustrated brushes 410 can be integrally molded, with the elongate rod 420 and the plurality of bristles 422, 424 forming a single co-molded structure having a common material. Preferably, as the bristles 422 have a narrower diameter than the elongate rods 420, the bristles have a greater degree of flexibility or deflection than the elongate rods.

The illustrated elongate rods 420 can have a tapering geometry, with a widest cross-sectional diameter at a fixed end 440 that is secured to the collar of the brush member 406, and a narrowest cross-sectional diameter at a free distal end 442.

The illustrated plurality of bristles are arranged in oppositely positioned pairs of outwardly extending bristles 422 and inwardly extending bristles 424. Each pair of outwardly 422 and inwardly 424 extending bristles are axially aligned with each other. The elongated rods 420 are positioned and oriented such that the pairs of bristles 422, 424 of each brush 410 is axially aligned with a similarly positioned pair in the opposing brush. The plurality of bristles 422, 424 on each brush 410 are oriented along a common plane extending from the fixed end 440 to the free end 442, with the outer bristles and the inner bristles being oriented along a common axial plane X, as specifically illustrated in FIG. 29. Accordingly, as the cleaning tool 400 is rotated during cleaning, the bristles 422, 424 across both brushes 410 form a single plane to consistently clean the connector 402.

As further illustrated, the bristles 422, 424 have fixed ends and free ends. The fixed ends are fixed to the outer surface of the elongated rods 420. The free ends extend away from the elongated rods, with the two illustrated sets of inwardly facing bristles 424 extending toward each other. The free ends of the bristles 422, 424 extend to a common distance from a longitudinal axis (not shown) along which the elongated rods 420 extend. As a result, since the elongated rods 420 are tapered, the length of the bristles 422, 424 varies with respect to the adjacent bristle from the fixed end 440 of the brush 410 to the free end 442. Specifically, the bristles 422, 424 are longer at the distal end 442 of the brush 410 where the diameter of the elongated rods 420 are narrowest, and are shortest at the fixed end 440 where the diameter of the elongated rods are widest. Additionally, the distance each bristles extend from the elongated rods 420 is longer for the outer facing bristles 422, as illustrated by line T, than the inner facing bristles 424, as illustrated by line V, in order to ensure that the outer facing bristles can adequately engage and clean the threaded inner surface of the connector 402, and the plunger 408 from the plunger member 404 can extend in between.

Figure 30:
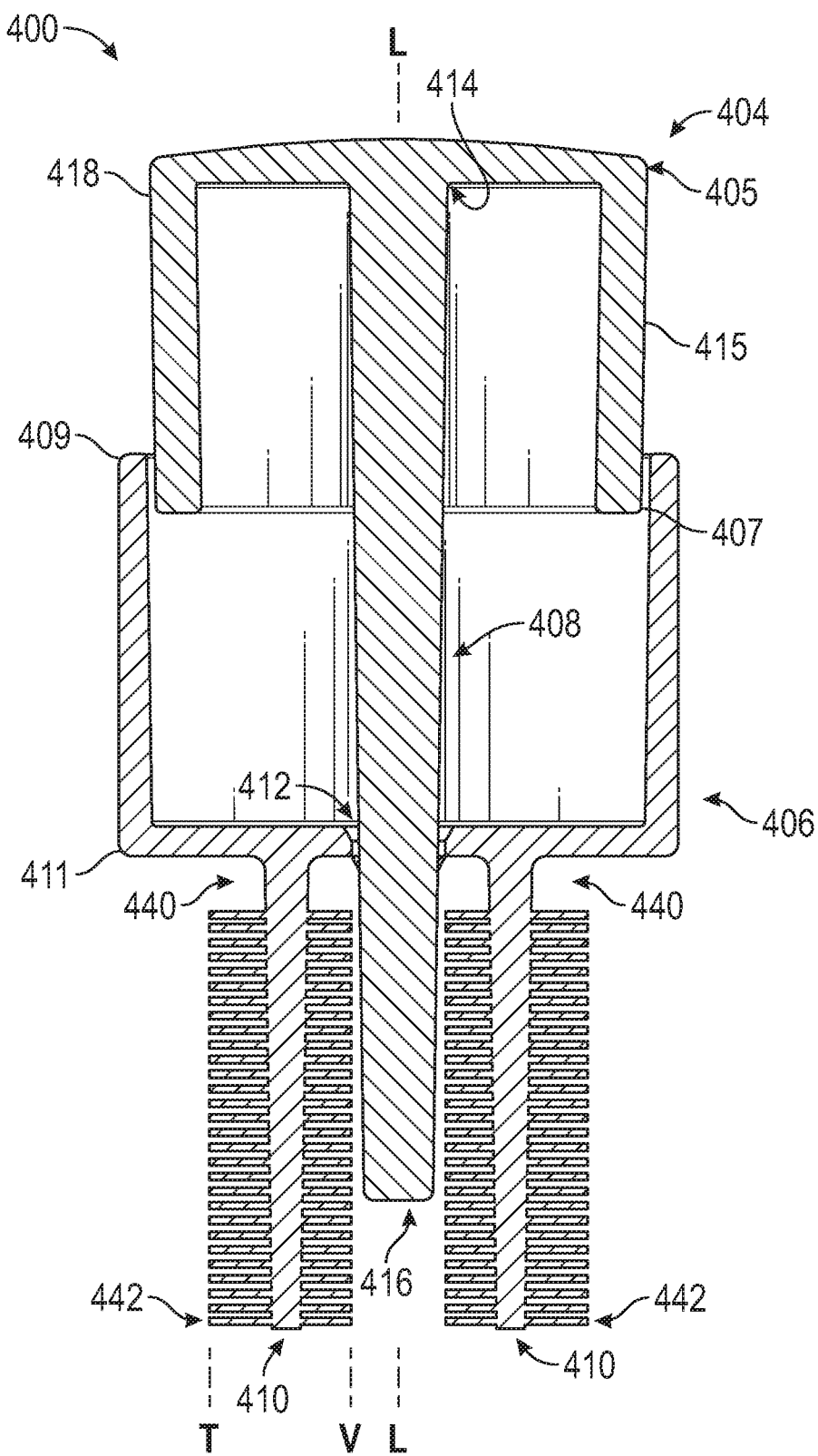
FIG. 30 is a cross-sectional view of the cleaning device shown in FIG. 27, as viewed along sight line A.
Figure 31:
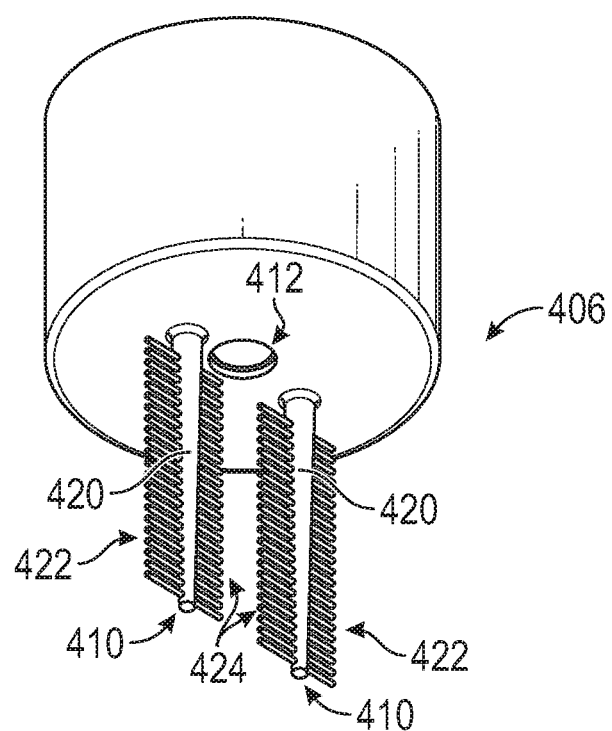
FIG. 31 is an isolated perspective view of the cleaning end of the brush portion of the cleaning device shown in FIG. 27.
Figure 32:
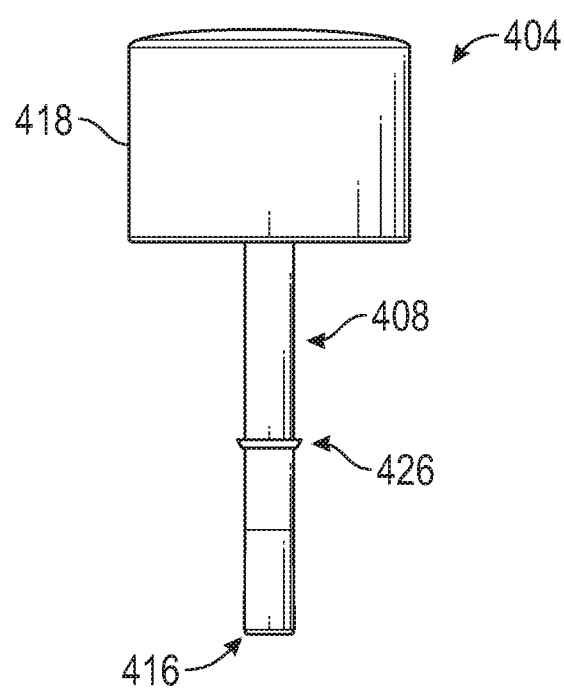
FIG. 32 is an isolated side view of the plug portion of the cleaning device shown in FIG. 27.
Figure 33:
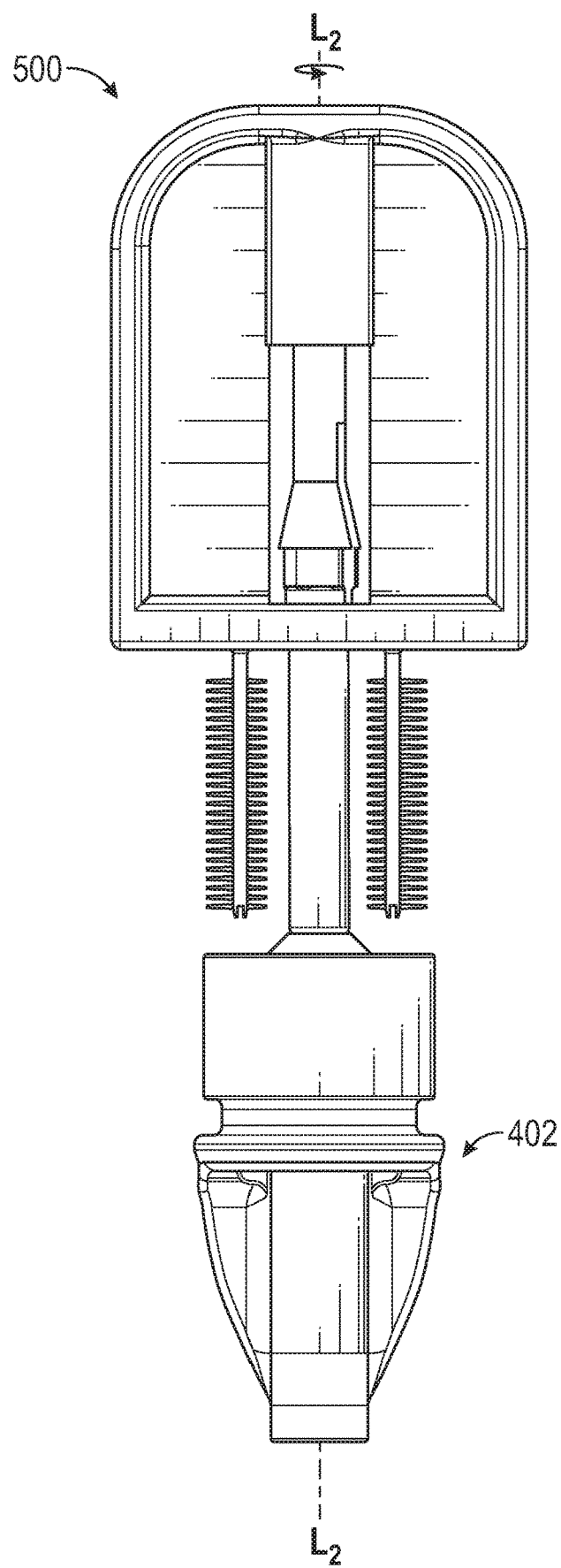
FIG. 33 is a plan view of a cleaning device for cleaning a connector, according to another example embodiment of the present invention, showing a schematic diagram of the cleaning tool in relation to a connector to be cleaned.
Figure 34:
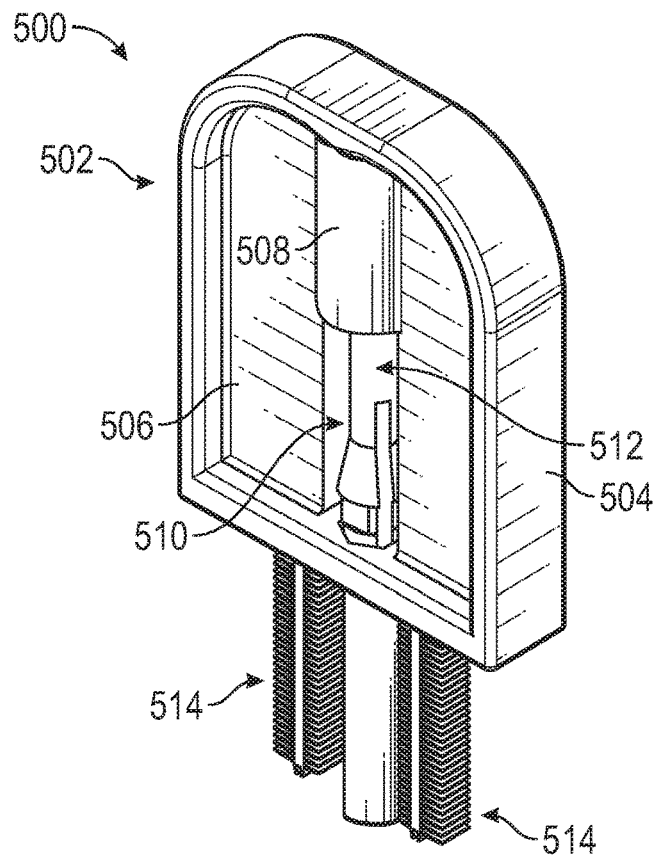
FIG. 34 is a perspective view of the cleaning device shown in FIG. 33.
Figure 35:
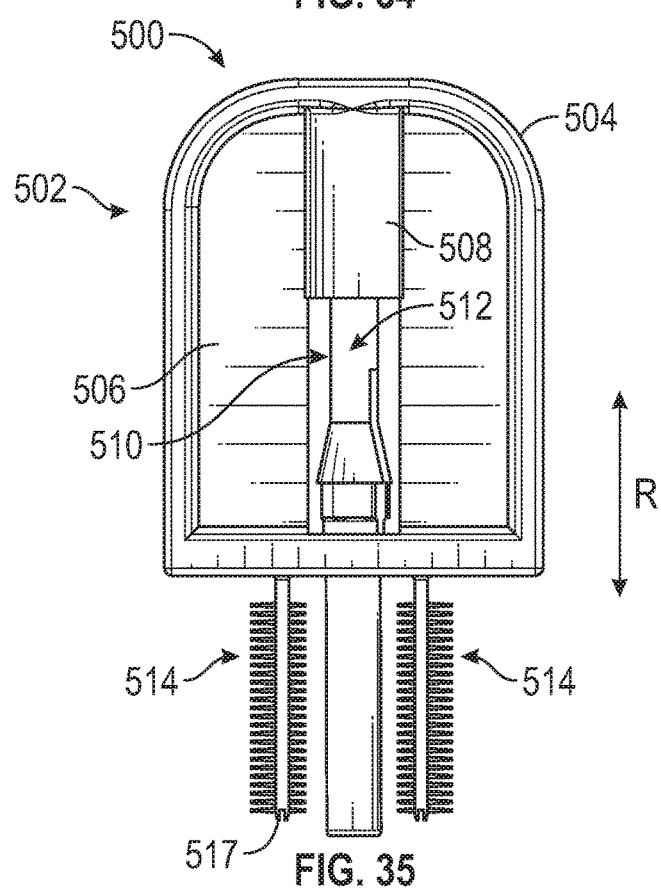
FIG. 35 is a plan view of the cleaning device shown in FIG. 33.

FIGS. 30 and 32 specifically illustrate the example plunger member 404. The plunger member 404 includes a collar 418 or handle, which can have a hollow interior. The plumber member 408 extends from a fixed end 414 at the top of the interior of the collar 418, to a free distal end or tip 416 that is configured for engaging a lumen in the connector 402. The plunger member 404 can be co-molded, such that the collar 418 and the elongated plunger 408 form a single structure.

As specifically illustrated in FIG. 30, the collar 418 of the plug member 404 can be defined by geometry and dimensions which allow for a friction fit within a receiver of the brush member 406. For example, the collar 418 can have an outer wall 415 that extends circumferentially between a fixed end 405 and a free end 407 defining an opening. As depicted, the outer wall 415 extends at an angle that is different than the connection axis L, for example the outer wall can be angled inwardly toward the connection axis from the fixed end 405 to the fixed end 407. As a result, the diameter of the outer wall 415 can be greater at the free end 405 than at the free end 407. Similarly, the collar of the brush member 406 can have an outer wall surface and an inner wall surface, extending from a fixed end 411 to a free end 409. Similarly to the collar wall 415 in the plunger member 404, the free end 409 of the brush member 406 defines receiver opening for receiving the plunger member. The inner wall of the collar of the brush member 406 can widen from the fixed end 411 to the free end 409, thus extending along an angle that is different from the connection axis L. In use, the oppositely angled orientations of the collars of the plunger member 404 and the brush member 406 engage each other, creating a friction fit as the plunger member collar is inserted into the brush member collar.

As further illustrated, the elongated plunger 408 can have a consistent outer diameter between the fixed end 414 and the flange or tab 426 and can have a tapering diameter between the flange or tab and the free end 416. As illustrated, the outer diameter of the free end 416 is narrower than the outer diameter at the tab 426, so that during assembly of the cleaning device 400, the free distal end 416 can be inserted through the central opening 412 in the brush member 406 and translate through until the tab 426 engages the central opening.

Figure 29:
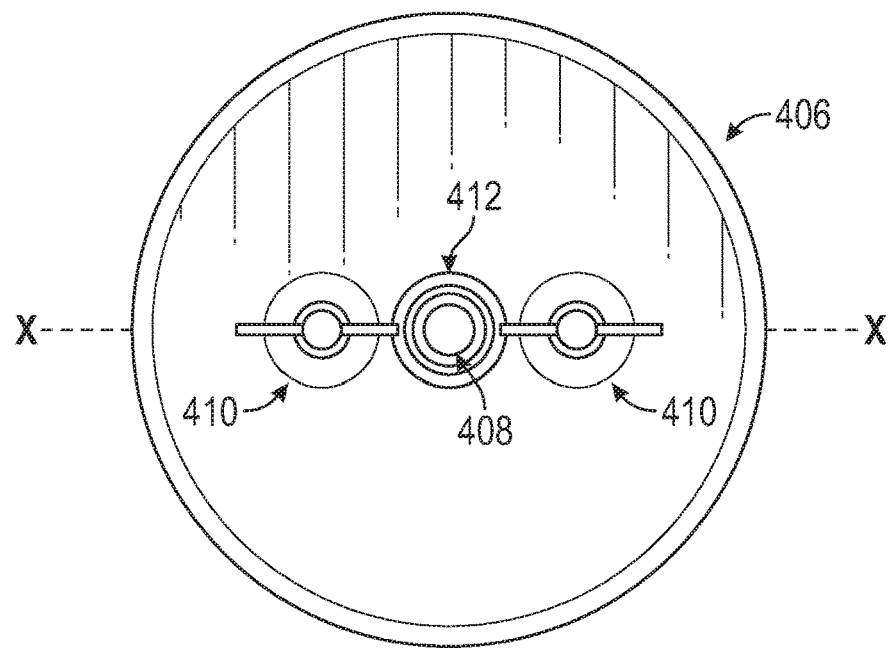
FIG. 29 is a cleaning end view of the cleaning device shown in FIG. 27.

As particularly shown in FIG. 29, when assembled, the plunger rod 408 is generally oriented between the brushes 410 along the common planar axis X.

In example embodiments, the bristles 422, 424 are generally elongate cylindrical members. In one example embodiment, the bristles 422, 424 comprise a diameter of about 0.229 millimeters, a length of between about 2.0 mm and about 2.3 mm, more preferably about 2.193 millimeters, and wherein the end-to-end length between oppositely-extending bristles is between about 4.8 mm and about 5.2 mm, more preferably about 4.957 millimeters. In example embodiments, the elongate rod 420 of each brush 410 comprises a length of between about 16.0 mm and about 17.0 mm, more preferably about 16.51 millimeters. In example embodiments, the outer diameter of the collar member of the brush member 406 is between about 19.0 mm and about 20.0 mm, more preferably about 19.5 millimeters. The outer diameter of the cap-like member 418 of the plunger member 404 is between about 17.0 mm and about 18.0 mm, more preferably about 17.365 millimeters. The elongate plunger rod 408 of the plunger member generally comprises a length of between about 35.0 mm and about 40.0 mm, more preferably about 35.50 millimeters, for example, wherein a free end 416 portion thereof comprises an outer diameter of about 2.523 millimeters and the fixed end opposite the free end comprises an outer diameter of about 3.918 millimeters. The outer flange 426 of the elongate plunger rod 408 comprises an outer diameter of between about 3.0 mm and about 4.0 mm, more preferably about 3.638 millimeters, for example, which is at least slightly larger than the central opening 412 formed in the brush member 406. In alternate embodiments, the brushes 410 can be configured as desired and can be dimensioned accordingly. According to some example embodiments, the brushes 410 can be configured to comprise bristles 422, 424 of various lengths and configurations. As described above, according to some example embodiments, the bristles extending outwardly 422 for engagement with the threads of the connector 402 can be generally longer than the bristles extending inwardly 424 for engagement with the male projection of the connector. According to some example embodiments, the brushes only comprise outwardly-extending bristles for engagement with the threaded collar. In other example embodiments, the brushes can comprise a plurality of bristles, for example, wherein at least some of the bristles are generally oriented to extend perpendicular relative to at least one other bristle on the same brush. In other example embodiments, the bristles can be configured for extending outwardly along a helical path around the entirety of the elongate rod, or for example, extending outwardly to define a plurality of spaced-apart radial segmented bristles. Optionally, other brush and bristle configurations can be chosen as desired.

FIGS. 33-39 illustrate a cleaning device 500 according to another example embodiment of the present invention. According to example embodiments, the cleaning device 500 comprises a plunger member 512 and a pair of brush member 502. The plunger member 512 comprises an elongate plunger rod that is configured for movably mounting with respect to the brush member 502. The brush member 502 comprises an upper grasping portion or handle which includes a planar portion 506 defined by a raised-ridge perimeter 504, a centrally-positioned receiver 508 for receiving the plunger member 512, and a pair of brushes 514 extending from a portion of the grasping member.

The illustrated brushes 514 comprise an elongated rod 522 supporting a pair of oppositely-extending inwardly 524 and outwardly 526 extending projections, for example, which are generally flat wedge-shaped members. The brushes 514 are integrally formed, for example through micro-molding, with the grasping portion formed by the planar portion 506 and the raised-ridge perimeter 504, for example, such that a single molded piece can be assembled with the plunger member. Similarly to the embodiment in FIGS. 27-32, the inwardly extending bristles 524 can extend a shorter distance from the elongated rod 522 than the outwardly facing bristles 526, so as to adequately clean the threaded inner surface of the connector 402, and to accommodate insertion of the plunger member 512. And, similarly to the embodiment in FIGS. 27-32, the outer distal ends of each bristle 524, 526 extends a common distance from the elongated rod 522 as the adjacent bristles, so as to form a consistent distal line or planar axis from the fixed end of the brush 514 to the free end of the brush.

As illustrated, the distal ends of the elongated rods 522 of each brush 514 can have a pair of teeth 517 which can function to clean out the bottom surface of the connector 402.

A receiver chamber 510 is illustrated to extend centrally through the brush member 502. The receiver chamber 510 is oriented along an axis that is co-axial with a connection axis $L_2$ of the cleaning device 500, shown in FIG. 33. The receiving chamber 510 includes a receiver 508 positioned in the planar portion 506, and an aperture 520 in a flat end 528 of the raised ridge 504. As illustrated, the aperture 520 can have a non-circular cross-sectional shape, for example a hexagon or other shape that will prevent a corresponding shape from rotating within the aperture. The receiver chamber 510 also defines a window or passage in the planar portion 506, extending through the planar portion between the receiver 508 and the aperture 520. The receiver 508 can have a hollow core with an open end facing the aperture 520, to receive an end of the plunger 512.

Optionally, as similarly described above, the brushes 514 and projections or bristles 524, 526 extending therefrom can be configured as desired, for example, comprising any desirable, shape, orientation, etc. For example, according to some embodiments, the bristles 524, 526 can project about 90 degrees relative to each other, or for example, be formed to extend along a helical path, or for example, comprise various lengths, cross-sectional shapes, etc.

Figure 39:
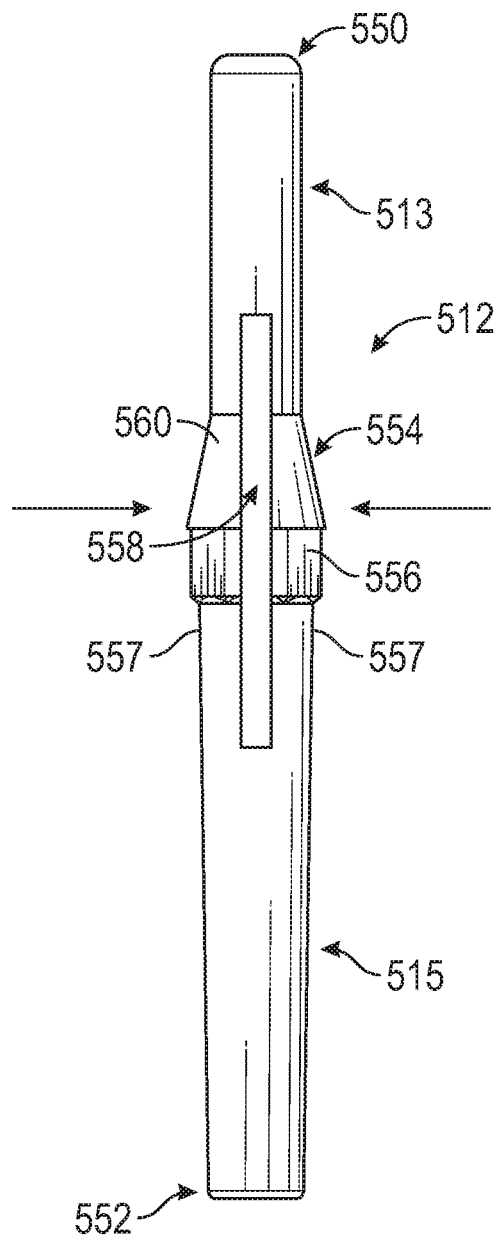
FIG. 39 is an isolated side view of the plug portion of the cleaning device shown in FIG. 34, shown without the brush portion.

As specifically illustrated in FIG. 39, the plunger member 512 comprises a generally elongated geometry defined by a retainer portion 513 and a plug portion 515. The distal end 550 of the retainer portion 513 is configured to be receivably inserted through aperture 520, and into the receiver 508. The distal end 552 of the plug portion 515 is configured to engage the lumen of the connector 402 during cleaning. Similarly to the plunger member 408 in the embodiment above, the receiver portion 513 can have a consistent outer diameter and the plunger portion 515 can have a tapered outer diameter with the narrowest diameter being at the distal end 552.

The illustrated plunger member 512 includes a centrally-positioned channel 558 extending therethrough, for example, which preferably allows for a transitional mid portion 554 of the plunger to flex inwardly to pass through the aperture 520 of the brush member 502. The channel 558 is defined by a pair of opposing flex walls 557 on either side. The transitional mid portion 554 comprises a tapered neck 560 with an overhang that is preferably, at a widest dimension, larger in dimension than the aperture 520, for example, such that the plunger 512 is retained with the brush member 502. After the distal receiver end 550 is inserted through the aperture 520, the receiver portion 513 is also inserted through the aperture until the neck engages the aperture, preventing further free insertion therethrough. A degree of force is applied to push the neck 560 against the aperture 520, thus creating a resistive force between the neck and the aperture. This resistive force causes the flex walls 557 on either side of the channel 558 to flex inwardly toward each other, thus also reducing the outer width of the neck 560 to a size that is slightly smaller than the aperture 520, such that the neck inserts past the aperture.

Figure 36:
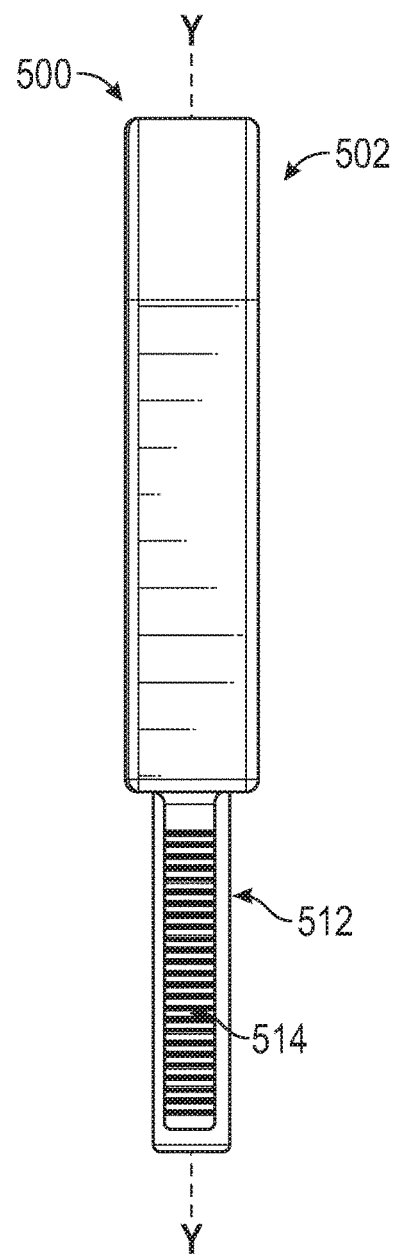
FIG. 36 is a side view of the cleaning device shown in FIG. 33.
Figure 37:
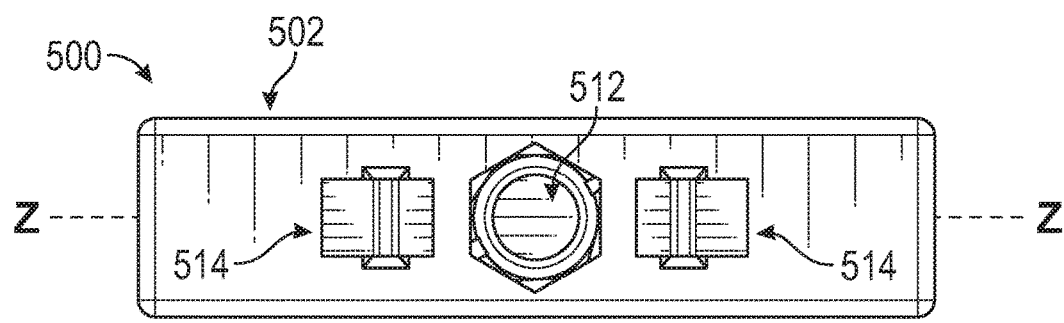
FIG. 37 is a cleaning end view of the cleaning device shown in FIG. 33.
Figure 38:
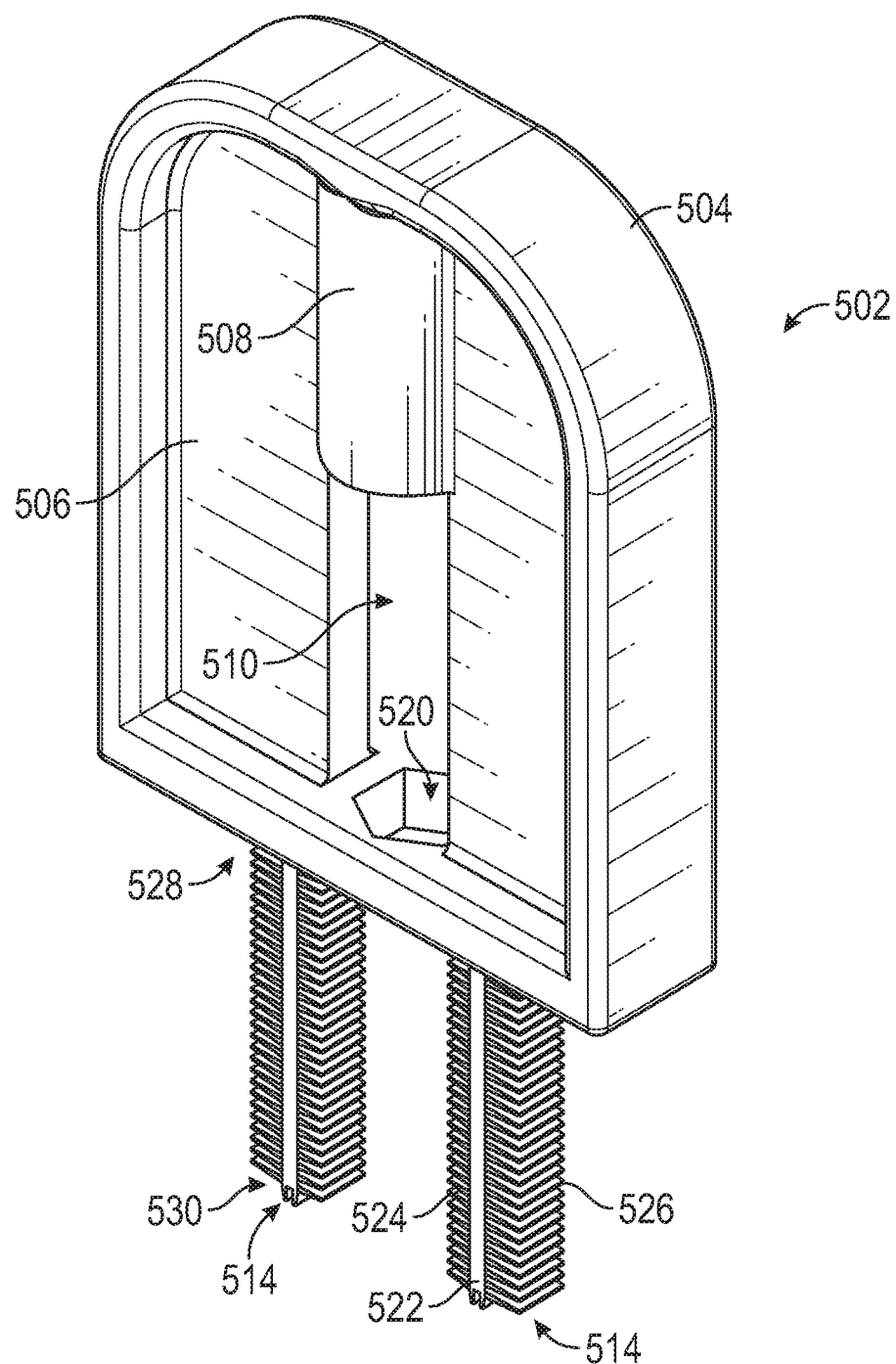
FIG. 38 is an isolated perspective view of the brush portion of the cleaning device shown in FIG. 34, shown without the plug portion.

As particularly illustrated in FIGS. 36 and 37, a key advantage of the cleaning device 500 is that when assembled together, the brush member 502 and the plunger member 512 are aligned along the common cleaning axis $L_2$ and are generally oriented along a common planar axis Z, such that when assembled, the cleaning device can be laid flat. This flat orientation can be achieved with the generally planar or flat geometry of the brush member 502.

When the distal receiver end 550 is inserted into the receiver 508, the receiver portion 513 can remain freely translational within the receiver along the connection axis, and freely rotatable within the receiver about the connection axis. Similarly, an upper section (when viewing FIG. 39) of the plunger portion 515 can also freely translate and rotate within the aperture 520. In use, the plug end 552 engages the lumen of the connector 402, and the user rotates the brush member 502 about the connection axis with the gripping members 504, 506.

Similarly to the embodiments described above, the plunger member 512 is configured for plugging the conduit of the male hub of the connector 402. Preferably the distal plunger end 552 is generally frictionally engaged with the conduit of the male hub when the brushes 514 are fitted within the collar of the connector 402. In some example embodiments, when it is desired to remove the brushes 514 from the collar of the connector 402, lifting up on the brush member 502, as shown generally with line R, causes a non-circular feature 556 of the plunger 512 to be fitted within the aperture of the brush member. Preferably, the geometry of the non-circular feature 556 of the plunger 512 corresponds with the non-circular geometry of the aperture 520 of the brush member 502, to prevent rotation of the plunger with respect to the brush member. Thus, to separate the cleaning device 500 from the connector 402, the brush member 502 is pulled away from the connector (and rotated relative thereto) to cause disengagement of the cleaning device from the connector.

Figure 40:
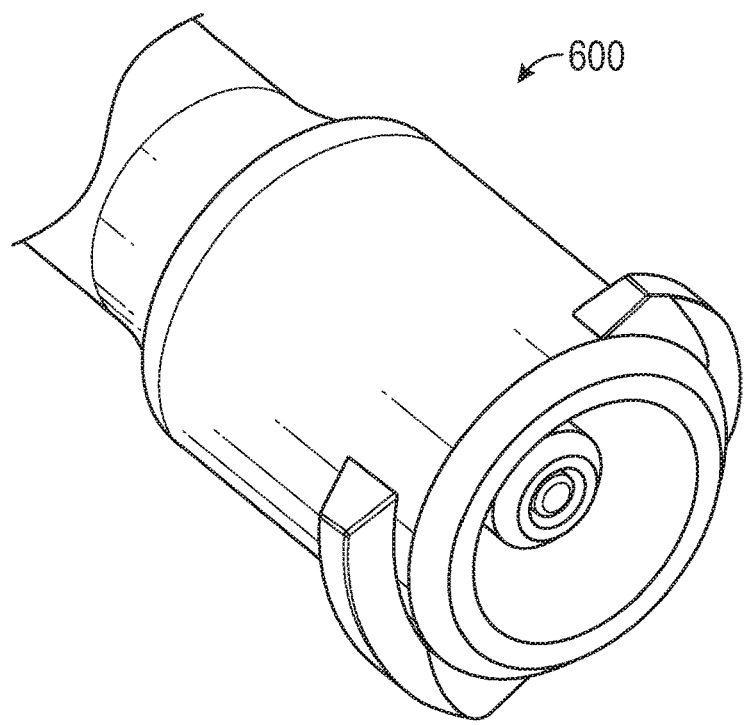
FIGS. 40-41 show cleaning devices according to additional example embodiments of the present invention.
Figure 41:
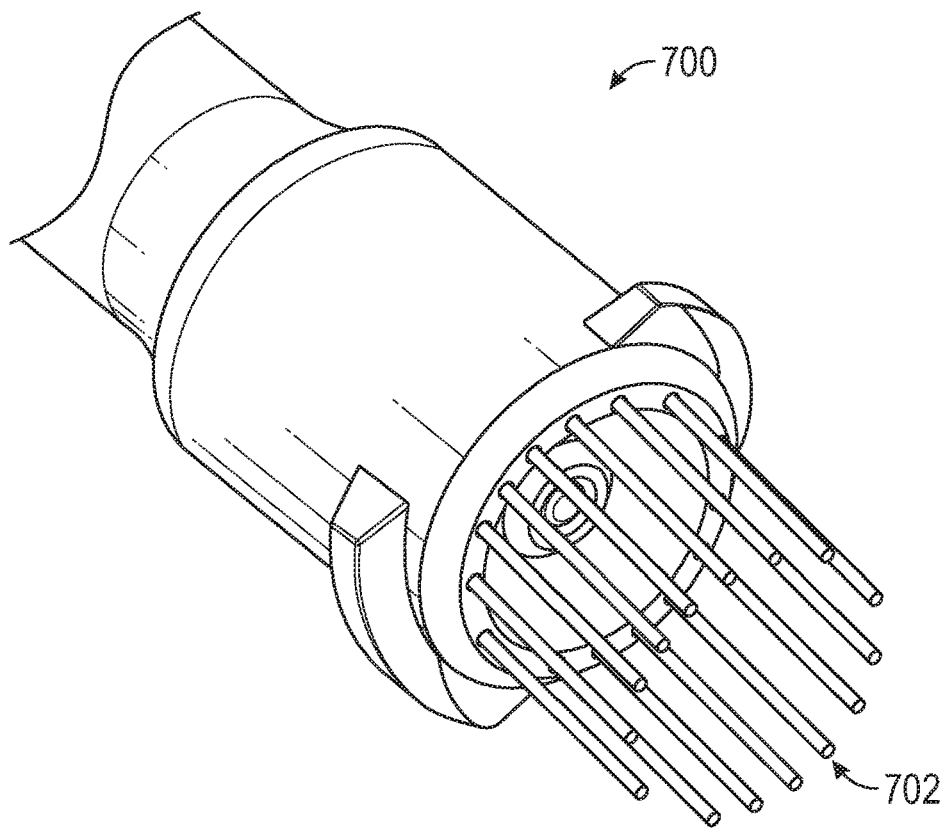

FIG. 40 illustrates a cleaning device 600 that is generally configured similarly to a female ENFit ISO 80369-3 formatted connector, for example, wherein the female connector comprises a threaded outer collar for engagement with the internal threads of the connector such that any residual feeding liquids or other debris retained within the connector are forcibly removed. According to some example embodiments, the female connector comprises a pair of lugs intended to move along the internal threads of the connector. In other example embodiments, the female connector is fully threaded. In some example embodiments, one or more additional projections can be provided on the female connector, for example, such that they further facilitate the removal of residual feeding liquids or other debris retained within the connector. FIG. 41 illustrates a cleaning device 700 generally similar to the cleaning device 600, but also including a plurality of projections or bristles 702 which extend from the end of the female connector. According to some example embodiments, the bristles 702 can comprise a plurality of flexible cleaning fingers or other micro projections to facilitate cleaning. In some example embodiments, one or more additional bristles can extend from the bristles of the female connector. For example, according to some example embodiments, additional bristles extends generally perpendicular (or at any desired angle) from the bristles.

Optionally, according to another example embodiment, the lugs or threads of the connector can comprise a plurality of bristles, for example, which generally project outwardly from the collar of the female connector and extend along a helical path. Thus, in example embodiments, the cleaning device comprises a threaded or lugged connector, for example, wherein the threads or lugs are formed from a plurality of bristles. Preferably, the bristles of the threads or lugs interengage with the threaded portion of the connector to provide for cleaning and debris removal. In some example embodiments, an inner portion or interior surface of the female connector can be provided to clean the male projection or hub of the connector.

While the invention has been described with reference to preferred and example embodiments, it will be understood by those skilled in the art that a variety of modifications, additions and deletions are within the scope of the invention, as defined by the following claims.

What is claimed is:

1. A cleaning device for cleaning a connector comprising a lumen and an inner threaded surface, the cleaning device comprising:
    a cleaning body and a plunger body operably coupled to each other, the cleaning body comprising a plurality of elongated cleaning brushes positioned separately apart from and in parallel to each other, the plurality of elongated cleaning brushes being operably rotatable about a connector lumen and in removable engagement with a connector inner threaded surface, the plunger body comprising an elongated plug to removably engage the connector lumen;
    wherein, the cleaning body and the plunger body are translatably coupled along a common operational axis, the cleaning body and the plunger body being rotatably coupled with respect to each other about the common operational axis, and wherein the cleaning body is an integral structure.

2. The cleaning device of claim 1, wherein the cleaning body and the plunger body are operably coupled to each other with a locking assembly.

3. The cleaning device of claim 2, wherein the locking assembly comprises a tab engaged with an aperture.

4. The cleaning device of claim 3, wherein the aperture extends through the cleaning body, and the tab projects outwardly from the plunger body elongated plug.

5. The cleaning device of claim 1, wherein the cleaning body elongated cleaning brushes comprise an elongated post and a plurality of bristles extending therefrom.

6. The cleaning device of claim 5, wherein the plunger body elongated plug is oriented in alignment with the common operational axis, and the cleaning body cleaning brush elongated posts are oriented in parallel to and offset from the common operational axis.

7. The cleaning device of claim 5, wherein the plurality of bristles extend from the elongated posts along a common planar axis.

8. The cleaning device of claim 7, wherein the plurality of bristles comprise a plurality of inner bristles extending inwardly toward the common operational axis, and a plurality of outer bristles extending outwardly away from the common operational axis.

9. The cleaning device of claim 8, wherein the outer bristles are longer than the inner bristles.

10. The cleaning device of claim 7, wherein the elongated plug is operably positioned along the common planar axis between the plurality of bristles.

11. The cleaning device of claim 1, further comprising a handle portion to cause operational rotation of the plurality of cleaning brushes about the common operational axis.

12. The cleaning device of claim 11, wherein the handle portion forms part of the cleaning body.

13. The cleaning device of claim 1, further comprising an anti-rotation assembly to releasably prevent rotation of the cleaning body with respect to the plunger body.

14. The cleaning device of claim 13, wherein the anti-rotation assembly comprises a non-circular aperture extending through the cleaning body, and a corresponding non-circular region positioned along the plunger body elongated plug.

15. The cleaning device of claim 1, wherein the cleaning body comprises a handle that defines a generally flat geometry, and the handle, the elongated plug and the plurality of cleaning brushes are positioned along a common planar axis.

16. A cleaning device for cleaning a connector comprising a lumen and a threaded inner surface, the cleaning device comprising:
    an elongated plunger comprising a retained end and a free end, the free end being configured to engage a connector lumen; and a brush body forming a single integral structure, the brush body comprising a gripping portion, a plunger receiver, and a plurality of brushes comprising an elongated post and a plurality of bristles extending therefrom, the plurality of bristles and the elongated plunger being oriented with respect to each other along a common planar axis;

wherein the brush body and the elongate plunger are translatably coupled along a common operational axis, the brush body and the elongated plunger being rotatably coupled with respect to each other about the common operational axis.

17. The cleaning device of claim 16, wherein the plurality of bristles comprises a plurality of inwardly facing bristles and a plurality of outwardly facing bristles, the plurality of inwardly facing bristles extending towards the elongated plunger.

18. The cleaning device of claim 17, wherein the plurality of inwardly facing bristles and the plurality of outwardly facing bristles are oriented along the common planar axis.

19. The cleaning device of claim 16, wherein the brush body gripping portion is generally flat.

* * * * *